United States Patent [19]
Van Aken

[11] Patent Number: 5,489,537
[45] Date of Patent: Feb. 6, 1996

[54] AGGLUTINATION ASSAYS AND KITS EMPLOYING COLLOIDAL DYES

[75] Inventor: Morgan Van Aken, Bainbridge Island, Wash.

[73] Assignee: Bainbridge Sciences, Inc., Redmond, Wash.

[21] Appl. No.: 23,906

[22] Filed: Feb. 23, 1993

Related U.S. Application Data

[63] Continuation-in-part of Ser. No. 806,908, Dec. 13, 1991, abandoned.

[51] Int. Cl.$^6$ .............. G01N 33/546; G01N 33/547; G01N 33/558; G01N 33/574
[52] U.S. Cl. .............. 436/534; 435/7.23; 435/970; 435/975; 436/514; 436/523; 436/533; 436/541; 436/161
[58] Field of Search .............. 436/514, 528, 436/531, 533, 534, 523, 536, 538, 539, 541, 64, 161, 162, 164, 169, 805, 824; 435/7.23, 970, 975; 530/388.8, 389.7

[56] References Cited

U.S. PATENT DOCUMENTS

| | | | |
|---|---|---|---|
| 3,802,842 | 4/1974 | Lange et al. | 435/28 |
| 4,373,932 | 2/1983 | Gribnau et al. | 436/531 |
| 4,419,453 | 12/1983 | Dorman et al. | 436/534 |
| 4,552,839 | 11/1985 | Gould et al. | 422/56 |
| 4,666,863 | 5/1987 | Edwards et al. | 436/533 |
| 4,918,164 | 4/1990 | Hellstrom et al. | 530/387.2 |
| 4,943,522 | 7/1990 | Eisinger et al. | 436/531 |

FOREIGN PATENT DOCUMENTS

WO90/07116  6/1990  WIPO.

OTHER PUBLICATIONS

Leigh B. Bangs, *Uniform Latex Particles*, (Indiana: Seragen Diagnostics Inc., 1984).
Donald E. Brooks et al., *Applying Latex–Based Technology in Diagnostics*, HSC Biotechnology Technical Report Series, HSC Short Course #104, ed. Geoffrey V. F. Seaman (Washington, D.C., Health & Sciences Communications 1990).
Yogi et al, 1991. Clinical Evaluation of Bladder Tumor Marker TU–MARK–BTA. Acta Urol Japan 37(4):335–9.

*Primary Examiner*—David Saunders
*Assistant Examiner*—James L. Grun
*Attorney, Agent, or Firm*—Seed and Berry

[57] ABSTRACT

The present invention provides methods and kits for determining the presence or amount of a substance by detection of a colloidal dye associated with agglutinated particles. The disclosure of the present invention shows that the use of a suspension of colloidal dye, which contains dye unattached to the particles to be agglutinated, enhances the amount of colloidal dye associated with the particles following agglutination. The methods and kits are disclosed in direct and indirect (e.g., competitive) formats. In one aspect, the present invention provides methods and kits utilizing a single colloidal dye. In another aspect, methods and kits are provided which include two colloidal dyes, wherein one colloidal dye functions as a background-enhancing dye. A related aspect of the present invention provides methods and kits that include a colloidal dye and a non-water-soluble dye (which functions as a background-enhancing dye) attached to a microporous pad which permits differential migration of non-agglutinated and agglutinated particles. In yet another aspect, the present invention provides methods and kits utilizing a colloidal dye and a water-soluble dye, which functions as a background-enhancing dye.

22 Claims, 4 Drawing Sheets

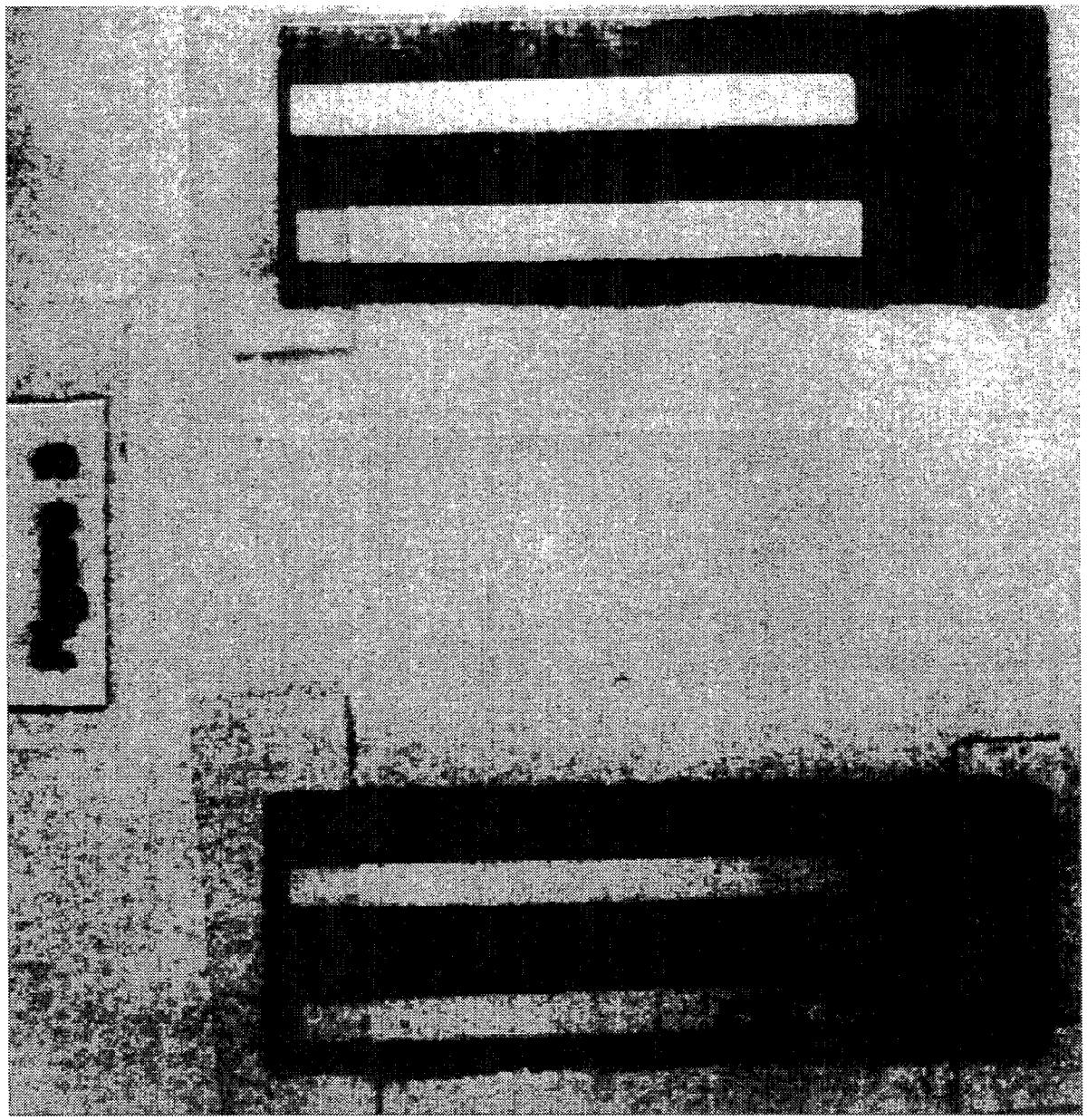

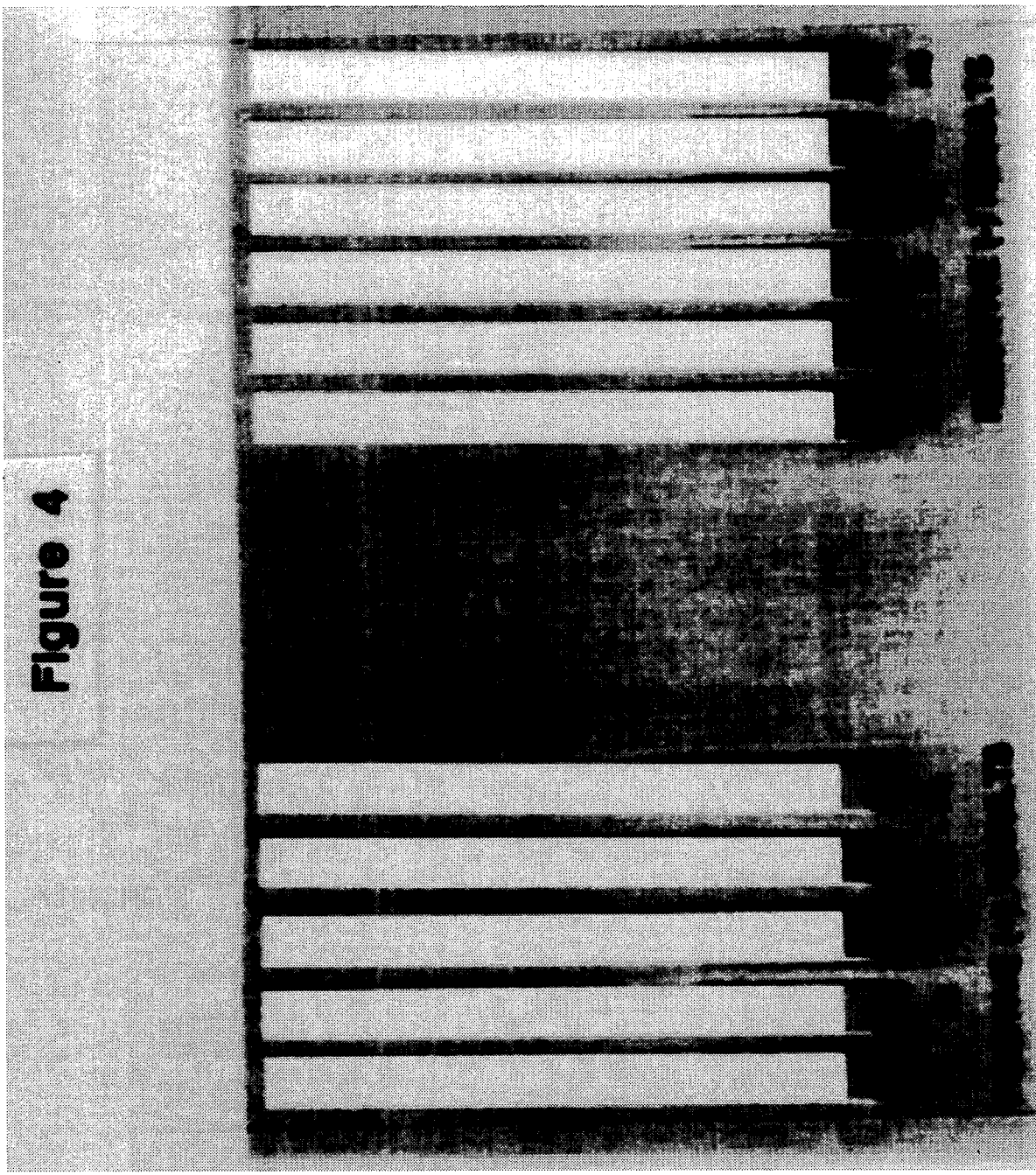

AGGLUTINATION ASSAYS AND KITS EMPLOYING COLLOIDAL DYES

CROSS-REFERENCE TO RELATED APPLICATION

This application is a continuation-in-part application to Ser. No. 07/806,908, filed Dec. 13, 1991, now abandoned.

TECHNICAL FIELD

The present invention relates generally to the detection of the presence or amount of substances using agglutination methods and kits. This invention is more particularly related to the use of colloidal dyes for the visualization or quantification of agglutinated particles and the use of microporous pads for substantially separating the agglutinated particles.

BACKGROUND OF THE INVENTION

Underlying all successful therapeutic approaches is the initial diagnosis of the particular disease. A challenge to medicine since its inception has been to conceive of methods that permit rapid and accurate detection of diseases. Despite advances in diagnostic technology over the years, the current techniques for the diagnosis of many diseases are often inadequate or cost prohibitive for wide scale application.

Many diagnostic techniques involve detection of specific substances which may be present, or at least elevated in concentration, in only the disease state. Typically, detection of a substance itself, a molecule which recognizes the substance, or a reaction between the substance and the molecule, necessitates amplification in order to produce detectable levels. One approach to amplification is to use polymer particles having a molecule which recognizes a substance bound thereto. Such particles, when in the presence of the substance, will clump together (also known as agglutination) from an otherwise homogeneous solution. Agglutination may be detectable by visualizing the clumped particles directly or indirectly via dyed particles.

Subsequent to the introduction of the first diagnostic latex agglutination test, a number of different latex agglutination tests have been developed. However, most of the latex slide tests can be difficult to interpret and the length of the required "hands on time" can lead to false positives (i.e., a result is obtained which indicates that a substance is present in a sample when in fact it is not). Other tests may be easier to interpret, but are costly to manufacture. Thus, there is a need in the art for detection assays and kits which are rapid, accurate, cost-effective, and convenient. The present invention fulfills these needs and further provides other related advantages.

SUMMARY OF THE INVENTION

Briefly stated, the present invention provides a variety of methods and kits for determining the presence or amount of a substance in a biological fluid. The methods and kits of the present invention may be in a direct or indirect test format.

In an aspect of the present invention, methods and kits are provided which include a colloidal dye. In one embodiment, the method comprises the steps of: (a) incubating a biological fluid suspected of containing the substance with a suspension of colloidal dye and latex particles having a binding partner to the substance bound thereto, the latex particles having the colloidal dye directly or indirectly attached thereto or both, to form a reaction mixture wherein latex particles binding the substance agglutinate, and wherein at least some unattached colloidal dye within said suspension is entrapped as a result of said agglutination; (b) contacting the reaction mixture with a microporous pad which permits differential migration of non-agglutinated latex particles versus agglutinated latex particles; and (c) detecting the presence or amount of the colloidal dye associated with the agglutinated latex particles, and therefrom determining the presence or amount of the substance.

In another embodiment, the method comprises the steps of: (a) incubating a biological fluid suspected of containing the substance with a suspension of colloidal dye and latex particles having a binding partner to the substance bound thereto, the latex particles not having the colloidal dye directly or indirectly attached thereto, to form a reaction mixture wherein latex particles binding the substance agglutinate, and wherein at least some unattached colloidal dye within said suspension is entrapped as a result of said agglutination; (b) contacting the reaction mixture with a microporous pad which permits differential migration of nonagglutinated latex particles versus agglutinated latex particles; and (c) detecting the presence or amount of the colloidal dye associated with the agglutinated latex particles, and therefrom determining the presence or amount of the substance.

In another embodiment, the method comprises the steps of: (a) incubating a biological fluid suspected of containing the substance with a binding partner to the substance, to form a first reaction mixture; (b) incubating the first reaction mixture with a suspension of colloidal dye and latex particles having the substance bound thereto, the latex particles having the colloidal dye attached directly or indirectly thereto or both, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of non-agglutinated latex particles versus agglutinated latex particles; and (d) detecting the presence or amount of the colloidal dye associated with the agglutinated latex particles, and therefrom determining the presence or amount of the substance.

In another embodiment, the method comprises the steps of: (a) incubating a biological fluid suspected of containing the substance with a binding partner to the substance, to form a first reaction mixture; (b) incubating the first reaction mixture with a suspension of colloidal dye and latex particles having the substance bound thereto, the latex particles not having the colloidal dye attached directly or indirectly thereto, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of non-agglutinated latex particles versus agglutinated latex particles; and (d) detecting the presence or amount of the colloidal dye associated with the agglutinated latex particles, and therefrom determining the presence or amount of the substance.

In yet another embodiment, the method comprises the steps of: (a) incubating a biological fluid suspected of containing the bladder tumor analyte associated with transitional cell carcinoma with a suspension of colloidal dye and latex particles having a blocking protein bound thereto, the latex particles having the colloidal dye directly or indirectly attached thereto or both, to form a reaction mixture wherein latex particles binding the analyte agglutinate, and wherein at least some unattached colloidal dye within said suspension is entrapped as a result of said agglutination; (b) contacting the reaction mixture with a microporous pad which permits differential migration of non-agglutinated latex particles versus agglutinated latex particles; and (c) detecting the presence or amount of the colloidal dye associated with the agglutinated latex particles, and therefrom determining the presence or amount of the analyte. In a related embodiment, the method comprises the steps of: (a) incubating a biological fluid suspected of containing the bladder tumor analyte associated with transitional cell carcinoma with a binding partner to the analyte, to form a first reaction mixture; (b) incubating the first reaction mixture with a suspension of colloidal dye and latex particles having the analyte bound thereto, the latex particles having the colloidal dye directly or indirectly attached thereto or both, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of nonagglutinated latex particles versus agglutinated latex particles; and (d) detecting the presence or amount of the colloidal dye associated with the agglutinated latex particles, and therefrom determining the presence or amount of the analyte.

In yet another embodiment, the method comprises the steps of: (a) incubating a biological fluid suspected of containing the bladder tumor analyte associated with transitional cell carcinoma with a suspension of colloidal dye and latex particles having a blocking protein bound thereto, the latex particles not having the colloidal dye directly or indirectly attached thereto, to form a reaction mixture wherein latex particles binding the analyte agglutinate, and wherein at least some unattached colloidal dye within said suspension is entrapped as a result of said agglutination; (b) contacting the reaction mixture with a microporous pad which permits differential migration of non-agglutinated latex particles versus agglutinated latex particles; and (c) detecting the presence or amount of the colloidal dye associated with the agglutinated latex particles, and therefrom determining the presence or amount of the analyte. In a related embodiment, the method comprises the steps of: (a) incubating a biological fluid suspected of containing the bladder tumor analyte associated with transitional cell carcinoma with a binding partner to the analyte, to form a first reaction mixture; (b) incubating the first reaction mixture with a suspension of colloidal dye and latex particles having the analyte bound thereto, the latex particles not having the colloidal dye directly or indirectly attached thereto, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of non-agglutinated latex particles versus agglutinated latex particles; and (d) detecting the presence or amount of the colloidal dye associated with the agglutinated latex particles, and therefrom determining the presence or amount of the analyte.

In one embodiment of a kit of the present invention, the kit comprises: (a) a suspension of colloidal dye and latex particles having a binding partner to the substance bound thereto, the latex particles having the colloidal dye directly or indirectly attached thereto or both; and (b) a microporous pad which permits differential migration of non-agglutinated latex particles versus agglutinated latex particles. In another embodiment, the kit comprises: (a) a binding partner to the substance; (b) a suspension of colloidal dye and latex particles having the substance bound thereto, the latex particles having the colloidal dye directly or indirectly attached thereto or both; and (c) a microporous pad which permits differential migration of non-agglutinated latex particles versus agglutinated latex particles.

In one embodiment of a kit of the present invention, the kit comprises: (a) a suspension of colloidal dye and latex particles having a binding partner to the substance bound thereto, the latex particles not having the colloidal dye directly or indirectly attached thereto; and (b) a microporous pad which permits differential migration of non-agglutinated latex particles versus agglutinated latex particles. In another embodiment, the kit comprises: (a) a binding partner to the substance; (b) a suspension of colloidal dye and latex particles having the substance bound thereto, the latex particles not having the colloidal dye directly or indirectly attached thereto; and (c) a microporous pad which permits differential migration of non-agglutinated latex particles versus agglutinated latex particles.

In yet another embodiment, the kit comprises: (a) a suspension of colloidal dye and latex particles having a blocking protein bound thereto, the latex particles having the colloidal dye directly or indirectly attached thereto or both; and (b) a microporous pad which permits differential migration of non-agglutinated latex particles versus agglutinated latex particles. Within a further embodiment, the kit comprises: (a) a binding partner to the analyte; (b) a suspension of colloidal dye and latex particles having the analyte bound thereto, the latex particles having the colloidal dye directly or indirectly attached thereto or both; and (c) a microporous pad which permits differential migration of non-agglutinated latex particles versus agglutinated latex particles.

In yet another embodiment, the kit comprises: (a) a suspension of colloidal dye and latex particles having a blocking protein bound thereto, the latex particles not having the colloidal dye directly or indirectly attached thereto; and (b) a microporous pad which permits differential migration of non-agglutinated latex particles versus agglutinated latex particles. Within a further embodiment, the kit comprises: (a) a binding partner to the analyte; (b) a suspension of colloidal dye and latex particles having the analyte bound thereto, the latex particles not having the colloidal dye directly or indirectly attached thereto; and (c) a microporous pad which permits differential migration of non-agglutinated latex particles versus agglutinated latex particles.

In another aspect, the present invention provides methods and kits which include two colloidal dyes. In one embodiment, the method comprises the steps of: (a) incubating a biological fluid suspected of containing the substance, latex particles having a first colloidal dye attached thereto, and a suspension of second colloidal dye and latex particles having a binding partner to the substance bound thereto and having the second colloidal dye attached directly or indirectly thereto or both, the first colloidal dye and the second colloidal dye being contrasting in color, to form a reaction mixture wherein latex particles binding the substance agglutinate, and wherein at least some unattached second colloidal dye within said suspension is entrapped as a result of said agglutination; (b) contacting the reaction mixture with a microporous pad which permits differential migration of non-agglutinated latex particles versus agglutinated latex particles; and (c) detecting the presence or amount of the second colloidal dye associated with the agglutinated latex particles, and therefrom determining the presence or amount of the substance. In another embodiment, the method comprises the steps of: (a) incubating a biological fluid suspected of containing the substance with a binding partner to the substance, to form a first reaction mixture; (b) incubating the first reaction mixture with latex particles having a first colloidal dye attached thereto and a suspension of second colloidal dye and latex particles having the substance bound thereto and having the second colloidal dye attached directly or indirectly thereto or both, the first colloidal dye and the second colloidal dye being contrasting in color, to form a second reaction mixture wherein latex particles binding the binding partner agglutinate, and wherein at least some unattached second colloidal dye within said suspension is entrapped as a result of said agglutination; (c) contacting the second reaction mixture with a microporous pad which permits differential migration of non-agglutinated latex particles versus agglutinated latex particles; and (d) detecting the presence or amount of the second colloidal dye associated with the agglutinated latex particles, and therefrom determining the presence or amount of the substance.

In one embodiment, the method comprises the steps of: (a) incubating a biological fluid suspected of containing the substance, latex particles having a first colloidal dye attached thereto, and a suspension of second colloidal dye and latex particles having a binding partner to the substance bound thereto and not having the second colloidal dye attached directly or indirectly thereto, the first colloidal dye and the second colloidal dye being contrasting in color, to form a reaction mixture wherein latex particles binding the substance agglutinate, and wherein at least some unattached second colloidal dye within said suspension is entrapped as a result of said agglutination; (b) contacting the reaction mixture with a microporous pad which permits differential migration of non-agglutinated latex particles versus agglutinated latex particles; and (c) detecting the presence or amount of the second colloidal dye associated with the agglutinated latex particles, and therefrom determining the presence or amount of the substance. In another embodiment, the method comprises the steps of: (a) incubating a biological fluid suspected of containing the substance with a binding partner to the substance, to form a first reaction mixture; (b) incubating the first reaction mixture with latex particles having a first colloidal dye attached thereto and a suspension of second colloidal dye and latex particles having the substance bound thereto and not having the second colloidal dye attached directly or indirectly thereto, the first colloidal dye and the second colloidal dye being contrasting in color, to form a second reaction mixture wherein latex particles binding the binding partner agglutinate, and wherein at least some unattached second colloidal dye within said suspension is entrapped as a result of said agglutination; (c) contacting the second reaction mixture with a microporous pad which permits differential migration of non-agglutinated latex particles versus agglutinated latex particles; and (d) detecting the presence or amount of the second colloidal dye associated with the agglutinated latex particles, and therefrom determining the presence or amount of the substance.

In yet another embodiment, the method comprises the steps of: (a) incubating a biological fluid suspected of containing the bladder tumor analyte associated with transitional cell carcinoma, latex particles having a first colloidal dye attached thereto, and a suspension of second colloidal dye and latex particles having a blocking protein bound thereto and having the second colloidal dye attached directly or indirectly thereto or both, the first colloidal dye and the second colloidal dye being contrasting in color, to form a reaction mixture wherein latex particles binding the analyte agglutinate, and wherein at least some unattached second colloidal dye within said suspension is entrapped as a result of said agglutination; (b) contacting the reaction mixture with a microporous pad which permits differential migration of non-agglutinated latex particles versus agglutinated latex particles; and (c) detecting the presence or amount of the second colloidal dye associated with the agglutinated latex particles, and therefrom determining the presence or amount of the analyte. Within a related embodiment, the method comprises the steps of: (a) incubating a biological fluid suspected of containing the bladder tumor analyte associated with transitional cell carcinoma with a binding partner to the analyte, to form a first reaction mixture; (b) incubating the first reaction mixture with latex particles having a first colloidal dye attached thereto and a suspension of second colloidal dye and latex particles having the analyte bound thereto and having the second colloidal dye attached directly or indirectly thereto or both, the first colloidal dye and the second colloidal dye being contrasting in color, to form a second reaction mixture wherein latex particles binding the binding partner agglutinate, and wherein at least some unattached second colloidal dye within said suspension is entrapped as a result of said agglutination; (c) contacting the second reaction mixture with a microporous pad which permits differential migration of non-agglutinated latex particles versus agglutinated latex particles; and (d) determining the presence or amount of the second colloidal dye associated with the agglutinated latex particles, and therefrom determining the presence or amount of the analyte.

In yet another embodiment, the method comprises the steps of: (a) incubating a biological fluid suspected of containing the bladder tumor analyte associated with transitional cell carcinoma, latex particles having a first colloidal dye attached thereto, and a suspension of second colloidal dye and latex particles having a blocking protein bound thereto and not having the second colloidal dye attached directly or indirectly thereto, the first colloidal dye and the second colloidal dye being contrasting in color, to form a reaction mixture wherein latex particles binding the analyte agglutinate, and wherein at least some unattached second colloidal dye within said suspension is entrapped as a result of said agglutination; (b) contacting the reaction mixture with a microporous pad which permits differential migration of non-agglutinated latex particles versus agglutinated latex particles; and (c) detecting the presence or amount of the second colloidal dye associated with the agglutinated latex particles, and therefrom determining the presence or amount of the analyte. Within a related embodiment, the method comprises the steps of: (a) incubating a biological fluid suspected of containing the bladder tumor analyte associated with transitional cell carcinoma with a binding partner to the analyte, to form a first reaction mixture; (b) incubating the first reaction mixture with latex particles having a first colloidal dye attached thereto and a suspension of second colloidal dye and latex particles having the analyte bound thereto and not having the second colloidal dye attached directly or indirectly thereto, the first colloidal dye and the second colloidal dye being contrasting in color, to form a second reaction mixture wherein latex particles binding the binding partner agglutinate, and wherein at least some unattached second colloidal dye within said suspension is entrapped as a result of said agglutination; (c) contacting the second reaction mixture with a microporous pad which permits differential migration of non-agglutinated latex particles versus agglutinated latex particles; and (d) determining the presence or amount of the second colloidal dye associated with the agglutinated latex particles, and therefrom determining the presence or amount of the analyte.

In one embodiment of a kit of the present invention, the kit comprises: (a) latex particles having a first colloidal dye attached thereto; (b) a suspension of second colloidal dye and latex particles having a binding partner to the substance bound thereto and having the second colloidal dye attached directly or indirectly thereto or both, the first colloidal dye and the second colloidal dye being contrasting in color; and (c) a microporous pad which permits differential migration of non-agglutinated latex particles versus agglutinated latex particles. In another embodiment, the kit comprises: (a) a binding partner to the substance; (b) latex particles having a first colloidal dye attached thereto; (c) a suspension of second colloidal dye and latex particles having the substance bound thereto and having the second colloidal dye attached directly or indirectly thereto or both, the first colloidal dye and the second colloidal dye being contrasting in color; and (d) a microporous pad which permits differential migration of non-agglutinated latex particles versus agglutinated latex particles.

In one embodiment of a kit of the present invention, the kit comprises: (a) latex particles having a first colloidal dye attached thereto; (b) a suspension of second colloidal dye and latex particles having a binding partner to the substance bound thereto and not having the second colloidal dye attached directly or indirectly thereto, the first colloidal dye and the second colloidal dye being contrasting in color; and (c) a microporous pad which permits differential migration of non-agglutinated latex particles versus agglutinated latex particles. In another embodiment, the kit comprises: (a) a binding partner to the substance; (b) latex particles having a first colloidal dye attached thereto; (c) a suspension of second colloidal dye and latex particles having the substance bound thereto and not having the second colloidal dye attached directly or indirectly thereto, the first colloidal dye and the second colloidal dye being contrasting in color; and (d) a microporous pad which permits differential migration of non-agglutinated latex particles versus agglutinated latex particles.

In yet another embodiment, the kit comprises: (a) latex particles having a first colloidal dye attached thereto; (b) a suspension of second colloidal dye and latex particles having a blocking protein bound thereto and having the second colloidal dye attached directly or indirectly thereto or both, the first colloidal dye and the second colloidal dye being contrasting in color; and (c) a microporous pad which permits differential migration of non-agglutinated latex particles versus agglutinated latex particles. In a further embodiment, the kit comprises: (a) a binding partner to the analyte; (b) latex particles having a first colloidal dye attached thereto; (c) a suspension of second colloidal dye and latex particles having the analyte bound thereto, and having the second colloidal dye attached directly or indirectly thereto or both, the first colloidal dye and the second colloidal dye being contrasting in color; and (d) a microporous pad which permits differential migration of nonoagglutinated latex particles versus agglutinated latex particles.

In yet another embodiment, the kit comprises: (a) latex particles having a first colloidal dye attached thereto; (b) a suspension of second colloidal dye and latex particles having a blocking protein bound thereto and not having the second colloidal dye attached directly or indirectly thereto, the first colloidal dye and the second colloidal dye being contrasting in color; and (c) a microporous pad which permits differential migration of non-agglutinated latex particles versus agglutinated latex particles. In a further embodiment, the kit comprises: (a) a binding partner to the analyte; (b) latex particles having a first colloidal dye attached thereto; (c) a suspension of second colloidal dye and latex particles having the analyte bound thereto, and not having the second colloidal dye attached directly or indirectly thereto, the first colloidal dye and the second colloidal dye being contrasting in color; and (d) a microporous pad which permits differential migration of non-agglutinated latex particles versus agglutinated latex particles.

In another aspect, the present invention provides methods and kits which include a colloidal dye and a non-water-soluble background-enhancing dye, the latter attached to a microporous pad. In one embodiment, the method comprises the steps of: (a) incubating a biological fluid suspected of containing the substance with a suspension of colloidal dye and latex particles having a binding partner to the substance bound thereto, the latex particles having the colloidal dye directly or indirectly attached thereto or both, to form a reaction mixture wherein latex particles binding the substance agglutinate, and wherein at least some unattached colloidal dye within said suspension is entrapped as a result of said agglutination; (b) contacting the reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (c) detecting the presence or amount of the colloidal dye associated with the agglutinated latex particles, and therefrom determining the presence or amount of the substance. In another embodiment, the method comprises the steps of: (a) incubating a biological fluid suspected of containing the substance with a binding partner to the substance, to form a first reaction mixture; (b) incubating the first reaction mixture with a suspension of colloidal dye and latex particles having the substance bound thereto, the latex particles having the colloidal dye directly or indirectly attached thereto or both, to form a second reaction mixture wherein latex particles binding the binding partner agglutinate, and wherein at least some unattached colloidal dye within said suspension is entrapped as a result of said agglutination; (c) contacting the second reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (d) detecting the presence or amount of the colloidal dye associated with the agglutinated latex particles, and therefrom determining the presence or amount of the substance.

In one embodiment, the method comprises the steps of: (a) incubating a biological fluid suspected of containing the substance with a suspension of colloidal dye and latex particles having a binding partner to the substance bound thereto, the latex particles not having the colloidal dye directly or indirectly attached thereto, to form a reaction mixture wherein latex particles binding the substance agglutinate, and wherein at least some unattached colloidal dye within said suspension is entrapped as a result of said agglutination; (b) contacting the reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (c) detecting the presence or amount of the colloidal dye associated with the agglutinated latex particles, and therefrom determining the presence or amount of the substance. In another embodiment, the method comprises the steps of: (a) incubating a biological fluid suspected of containing the substance with a binding partner to the substance, to form a first reaction mixture; (b) incubating the first reaction mixture with a suspension of colloidal dye and latex particles having the substance bound thereto, the latex particles not having the colloidal dye directly or indirectly attached thereto, to form a second reaction mixture wherein latex particles binding the binding partner agglutinate, and wherein at least some unattached colloidal dye within said suspension is entrapped as a result of said agglutination; (c) contacting the second reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (d) detecting the presence or amount of the colloidal dye associated with the agglutinated latex particles, and therefrom determining the presence or amount of the substance.

Within yet another embodiment, the method comprises the steps of: (a) incubating a biological fluid suspected of containing the bladder tumor analyte associated with transitional cell carcinoma with a suspension of colloidal dye and latex particles having a blocking protein bound thereto, the latex particles having the colloidal dye directly or indirectly attached thereto or both, to form a reaction mixture wherein latex particles binding the analyte agglutinate, and wherein at least some unattached colloidal dye within said suspension is entrapped as a result of said agglutination; (b) contacting the reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (c) detecting the presence or amount of the colloidal dye associated with the agglutinated latex particles, and therefrom determining the presence or amount of the analyte. In a related embodiment, the method comprises the steps of: (a) incubating a biological fluid suspected of containing the bladder tumor analyte associated with transitional cell carcinoma with a binding partner to the analyte, to form a first reaction mixture; (b) incubating the first reaction mixture with a suspension of colloidal dye and latex particles having the analyte bound thereto, the latex particles having the colloidal dye directly or indirectly attached thereto or both, to form a second reaction mixture wherein latex particles binding the binding partner agglutinate, and wherein at least some unattached colloidal dye within said suspension is entrapped as a result of said agglutination; (c) contacting the second reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (d) detecting the presence or amount of the colloidal dye associated with the agglutinated latex particles, and therefrom determining the presence or amount of the analyte.

Within yet another embodiment, the method comprises the steps of: (a) incubating a biological fluid suspected of containing the bladder tumor analyte associated with transitional cell carcinoma with a suspension of colloidal dye and latex particles having a blocking protein bound thereto, the latex particles not having the colloidal dye directly or indirectly attached thereto, to form a reaction mixture wherein latex particles binding the analyte agglutinate, and wherein at least some unattached colloidal dye within said suspension is entrapped as a result of said agglutination; (b) contacting the reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (c) detecting the presence or amount of the colloidal dye associated with the agglutinated latex particles, and therefrom determining the presence or amount of the analyte. In a related embodiment, the method comprises the steps of: (a) incubating a biological fluid suspected of containing the bladder tumor analyte associated with transitional cell carcinoma with a binding partner to the analyte, to form a first reaction mixture; (b) incubating the first reaction mixture with a suspension of colloidal dye and latex particles not having the analyte bound thereto, the latex particles not having the colloidal dye directly or indirectly attached thereto, to form a second reaction mixture wherein latex particles binding the binding partner agglutinate, and wherein at least some unattached colloidal dye within said suspension is entrapped as a result of said agglutination; (c) contacting the second reaction mixture with a microporous pad to which is attached a non-water-soluble background-enhancing dye that is contrasting in color to the colloidal dye, the microporous pad permitting differential migration of non-agglutinated latex particles versus agglutinated latex particles; and (d) detecting the presence or amount of the colloidal dye associated with the agglutinated latex particles, and therefrom determining the presence or amount of the analyte.

In one embodiment of a kit of the present invention, the kit comprises: (a) a suspension of colloidal dye and latex particles having a binding partner to the substance bound thereto, the latex particles having the colloidal dye directly or indirectly attached thereto or both; and (b) a microporous pad to which is attached a non-water-soluble background-enhancing dye that is contrasting in color to the colloidal dye, the microporous pad permitting differential migration of non-agglutinated latex particles versus agglutinated latex particles. In another embodiment, the kit comprises: (a) a binding partner to the substance; (b) a suspension of colloidal dye and latex particles having the substance bound thereto, the latex particles having the colloidal dye directly or indirectly attached thereto or both; and (c) a microporous pad to which is attached a non-water-soluble background-enhancing dye that is contrasting in color to the colloidal dye, the microporous pad permitting differential migration of non-agglutinated latex particles versus agglutinated latex particles.

In one embodiment of a kit of the present invention, the kit comprises: (a) a suspension of colloidal dye and latex particles having a binding partner to the substance bound thereto, the latex particles not having the colloidal dye directly or indirectly attached thereto; and (b) a microporous pad to which is attached a non-water-soluble background-enhancing dye that is contrasting in color to the colloidal dye, the microporous pad permitting differential migration of non-agglutinated latex particles versus agglutinated latex particles. In another embodiment, the kit comprises: (a) a binding partner to the substance; (b) a suspension of colloidal dye and latex particles having the substance bound thereto, the latex particles not having the colloidal dye directly or indirectly attached thereto or both; and (c) a microporous pad to which is attached a non-water-soluble background-enhancing dye that is contrasting in color to the colloidal dye, the microporous pad permitting differential migration of non-agglutinated latex particles versus agglutinated latex particles.

Within yet another embodiment, the kit comprises: (a) a suspension of colloidal dye and latex particles having a blocking protein bound thereto, the latex particles having the colloidal dye directly or indirectly attached thereto or both; and (b) a microporous pad to which is attached a non-water-soluble background-enhancing dye that is contrasting in color to the colloidal dye, the microporous pad permitting differential migration of non-agglutinated latex particles versus agglutinated latex particles. In a further embodiment, the kit comprises: (a) a binding partner to the analyte; (b) a suspension of colloidal dye and latex particles having the analyte bound thereto, the latex particles having the colloidal dye directly or indirectly attached thereto or both; and (c) a microporous pad to which is attached a non-water-soluble background-enhancing dye that is contrasting in color to the colloidal dye, the microporous pad permitting differential migration of non-agglutinated latex particles versus agglutinated latex particles.

Within yet another embodiment, the kit comprises: (a) a suspension of colloidal dye and latex particles having a blocking protein bound thereto, the latex particles not having the colloidal dye directly or indirectly attached thereto; and (b) a microporous pad to which is attached a non-water-soluble background-enhancing dye that is contrasting in color to the colloidal dye, the microporous pad permitting differential migration of non-agglutinated latex particles versus agglutinated latex particles. In a further embodiment, the kit comprises: (a) a binding partner to the analyte; (b) a suspension of colloidal dye and latex particles having the analyte bound thereto, the latex particles not having the colloidal dye directly or indirectly attached thereto; and (c) a microporous pad to which is attached a non-water-soluble background-enhancing dye that is contrasting in color to the colloidal dye, the microporous pad permitting differential migration of non-agglutinated latex particles versus agglutinated latex particles.

In another aspect, the present invention provides methods and kits which include a colloidal dye and a water-soluble background-enhancing dye. In one embodiment, the method comprises the steps of: (a) incubating a water-soluble background-enhancing dye, a biological fluid suspected of containing the substance, and a suspension of colloidal dye and latex particles having a binding partner to the substance bound thereto, the latex particles having the colloidal dye directly or indirectly attached thereto or both, the colloidal dye and the background-enhancing dye being contrasting in color, to form a reaction mixture wherein latex particles binding the substance agglutinate, and wherein at least some unattached colloidal dye within said suspension is entrapped as a result of said agglutination; (b) contacting the reaction mixture with a microporous pad which permits differential migration of non-agglutinated latex particles and background-enhancing dye versus agglutinated latex particles; and (c) detecting the presence or amount of the colloidal dye associated with the agglutinated latex particles, and therefrom determining the presence or amount of the substance. In another embodiment, the method comprises the steps of: (a) incubating a water-soluble background-enhancing dye, a biological fluid suspected of containing the substance, and a binding partner to the substance, to form a first reaction mixture; (b) incubating the first reaction mixture with a suspension of colloidal dye and latex particles having the substance bound thereto, the latex particles having the colloidal dye directly or indirectly attached thereto or both, the colloidal dye and the background-enhancing dye being contrasting in color, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of non-agglutinated latex particles and background-enhancing dye versus agglutinated latex particles; and (d) detecting the presence or amount of the colloidal dye associated with the agglutinated latex particles, and therefrom determining the presence or amount of the substance.

In another aspect, the present invention provides methods and kits which include a colloidal dye and a water-soluble background-enhancing dye. In one embodiment, the method comprises the steps of: (a) incubating a water-soluble background-enhancing dye, a biological fluid suspected of containing the substance, and a suspension of colloidal dye and latex particles having a binding partner to the substance bound thereto, the latex particles not having the colloidal dye directly or indirectly attached thereto, the colloidal dye and the background-enhancing dye being contrasting in color, to form a reaction mixture wherein latex particles binding the substance agglutinate, and wherein at least some unattached colloidal dye within said suspension is entrapped as a result of said agglutination; (b) contacting the reaction mixture with a microporous pad which permits differential migration of non-agglutinated latex particles and background enhancing dye versus agglutinated latex particles; and (c) detecting the presence or amount of the colloidal dye associated with the agglutinated latex particles, and therefrom determining the presence or amount of the substance. In another embodiment, the method comprises the steps of: (a) incubating a water-soluble background-enhancing dye, a biological fluid suspected of containing the substance, and a binding partner to the substance, to form a first reaction mixture; (b) incubating the first reaction mixture with a suspension of colloidal dye and latex particles having the substance bound thereto, the latex particles not having the colloidal dye directly or indirectly attached thereto, the colloidal dye and the background-enhancing dye being contrasting in color, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of non-agglutinated latex particles and background-enhancing dye versus agglutinated latex particles; and (d) detecting the presence or amount of the colloidal dye associated with the agglutinated latex particles, and therefrom determining the presence or amount of the substance.

In yet another embodiment, the method comprises the steps of: (a) incubating a water-soluble background-enhancing dye, a biological fluid suspected of containing the bladder tumor analyte associated with transitional cell carcinoma, and a suspension of colloidal dye and latex particles having a blocking protein bound thereto, the latex particles having the colloidal dye directly or indirectly attached thereto or both, the colloidal dye and the background-enhancing dye being contrasting in color, to form a reaction mixture wherein latex particles binding the analyte agglutinate, and wherein at least some unattached colloidal dye within said suspension is entrapped as a result of said agglutination; (b) contacting the reaction mixture with a microporous pad which permits differential migration of non-agglutinated latex particles and background-enhancing dye versus agglutinated latex particles; and (c) detecting the presence or amount of the colloidal dye associated with the agglutinated latex particles, and therefrom determining the presence or amount of the analyte. In a related embodiment, the method comprises the steps of: (a) incubating a water-soluble background-enhancing dye, a biological fluid suspected of containing the bladder tumor analyte associated with transitional cell carcinoma, and a binding partner to the analyte, to form a first reaction mixture; (b) incubating the first reaction mixture with a suspension of colloidal dye and latex particles having the analyte bound thereto, the latex particles having the colloidal dye directly or indirectly attached thereto or both, the colloidal dye and the background-enhancing dye being contrasting in color, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of non-agglutinated latex particles and background-enhancing dye versus agglutinated latex particles; and (d) detecting the presence or amount of the colloidal dye associated with the agglutinated latex particles, and therefrom determining the presence or amount of the analyte.

In yet another embodiment, the method comprises the steps of: (a) incubating a water-soluble background-enhancing dye, a biological fluid suspected of containing the bladder tumor analyte associated with transitional cell carcinoma, and a suspension of colloidal dye and latex particles having a blocking protein bound thereto, the latex particles not having the colloidal dye directly or indirectly attached thereto, the colloidal dye and the background-enhancing dye being contrasting in color, to form a reaction mixture wherein latex particles binding the analyte agglutinate, and wherein at least some unattached colloidal dye within said suspension is entrapped as a result of said agglutination; (b) contacting the reaction mixture with a microporous pad which permits differential migration of non-agglutinated latex particles and background-enhancing dye versus agglutinated latex particles; and (c) detecting the presence or amount of the colloidal dye associated with the agglutinated latex particles, and therefrom determining the presence or amount of the analyte. In a related embodiment, the method comprises the steps of: (a) incubating a water-soluble background-enhancing dye, a biological fluid suspected of containing the bladder tumor analyte associated with transitional cell carcinoma, and a binding partner to the analyte, to form a first reaction mixture; (b) incubating the first reaction mixture with a suspension of colloidal dye and latex particles having the analyte bound thereto, the latex particles not having the colloidal dye directly or indirectly attached thereto, the colloidal dye and the background-enhancing dye being contrasting in color, to form a second reaction mixture wherein latex particles binding the binding partner agglutinate, and wherein at least some unattached colloidal dye within said suspension is entrapped as a result of said agglutination; (c) contacting the second reaction mixture with a microporous pad which permits differential migration of non-agglutinated latex particles and background-enhancing dye versus agglutinated latex particles; and (d) detecting the presence or amount of the colloidal dye associated with the agglutinated latex particles, and therefrom determining the presence or amount of the analyte.

In one embodiment of a kit of the present invention, the kit comprises: (a) a water-soluble background-enhancing dye; (b) a suspension of colloidal dye and latex particles having a binding partner to the substance bound thereto, the latex particles having the colloidal dye directly or indirectly attached thereto or both, the colloidal dye and the background-enhancing dye being contrasting in color; and (c) a microporous pad which permits differential migration of non-agglutinated latex particles and background-enhancing dye versus agglutinated latex particles. In another embodiment, the kit comprises: (a) a binding partner to the substance; (b) a water-soluble background-enhancing dye; (c) a suspension of colloidal dye and latex particles having the substance bound thereto, the latex particles having the colloidal dye directly or indirectly attached thereto or both, the colloidal dye and the background-enhancing dye being contrasting in color; and (d) a microporous pad which permits differential migration of non-agglutinated latex particles and background-enhancing dye versus agglutinated latex particles.

In one embodiment of a kit of the present invention, the kit comprises: (a) a water-soluble background-enhancing dye; (b) a suspension of colloidal dye and latex particles having a binding partner to the substance bound thereto, the latex particles not having the colloidal dye directly or indirectly attached thereto, the colloidal dye and the background-enhancing dye being contrasting in color; and (c) a microporous pad which permits differential migration of non-agglutinated latex particles and background-enhancing dye versus agglutinated latex particles. In another embodiment, the kit comprises: (a) a binding partner to the substance; (b) a water-soluble background-enhancing dye; (c) a suspension of colloidal dye and latex particles having the substance bound thereto, the latex particles not having the colloidal dye directly or indirectly attached thereto, the colloidal dye and the background-enhancing dye being contrasting in color; and (d) a microporous pad which permits differential migration of non-agglutinated latex particles and background-enhancing dye versus agglutinated latex particles.

In yet another embodiment, the kit comprises: (a) a water-soluble background-enhancing dye; (b) a suspension of colloidal dye and latex particles having a blocking protein bound thereto, the latex particles having the colloidal dye directly or indirectly attached thereto or both, the colloidal dye and the background-enhancing dye being contrasting in color; and (c) a microporous pad which permits differential migration of non-agglutinated latex particles and background-enhancing dye versus agglutinated latex particles. In a further embodiment, the kit comprises: (a) a binding partner to the analyte; (b) a water-soluble background-enhancing dye; (c) a suspension of colloidal dye and latex particles having the substance bound thereto, the latex particles having the colloidal dye directly or indirectly attached thereto or both, the colloidal dye and the background-enhancing dye being contrasting in color; and (d) a microporous pad which permits differential migration of non-agglutinated latex particles and background-enhancing dye versus agglutinated latex particles.

In yet another embodiment, the kit comprises: (a) a water-soluble background-enhancing dye; (b) a suspension of colloidal dye and latex particles having a blocking protein bound thereto, the latex particles not having the colloidal dye directly or indirectly attached thereto, the colloidal dye and the background-enhancing dye being contrasting in color; and (c) a microporous pad which permits differential migration of non-agglutinated latex particles and background-enhancing dye versus agglutinated latex particles. In a further embodiment, the kit comprises: (a) a binding partner to the analyte; (b) a water-soluble background-enhancing dye; (c) a suspension of colloidal dye and latex particles having the substance bound thereto, the latex particles not having the colloidal dye directly or indirectly attached thereto, the colloidal dye and the background-enhancing dye being contrasting in color; and (d) a microporous pad which permits differential migration of non-agglutinated latex particles and background-enhancing dye versus agglutinated latex particles.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 3 pictorially depicts the results of an RF agglutination assay using a colloidal dye (Brilliant Blue R) and a non-water-soluble background-enhancing dye (Methyl Yellow) attached to a microporous pad. The assay was performed according to the procedures described in Example 4.

FIG. 4 pictorially depicts the results of an agglutination assay for a bladder tumor analyte (BTA) associated with transitional cell carcinoma of the bladder using a colloidal dye (Brilliant Blue R) and a water-soluble background-enhancing dye (Crescent Yellow). The assay was performed according to the procedures described in Example 7.

DETAILED DESCRIPTION OF THE INVENTION

Figure 1:
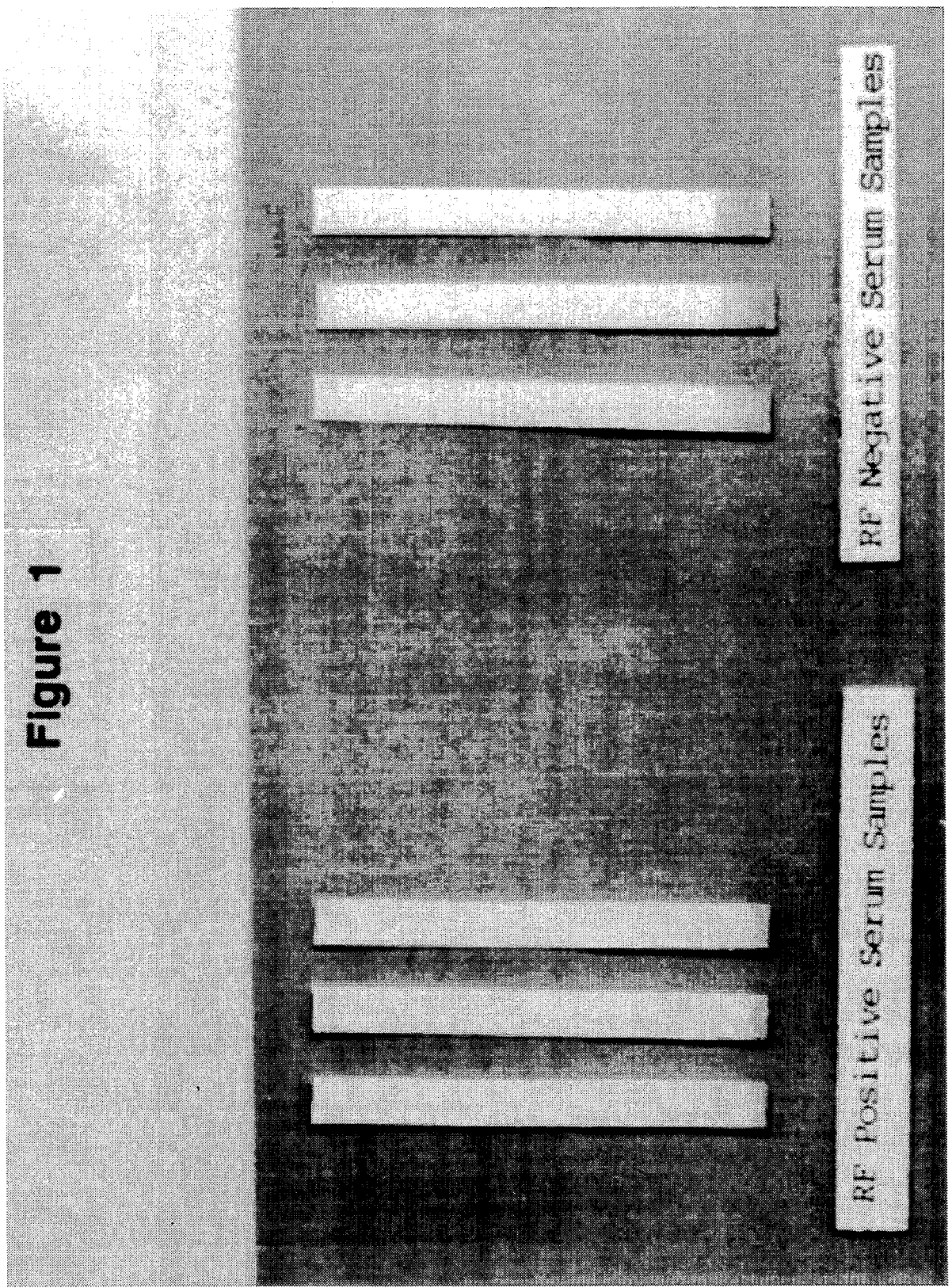
FIG. 1 pictorially depicts the results of an agglutination assay for rheumatoid factor (RF) using a single colloidal dye. The assay was performed according to the procedures described in Example 1, except Safranin O was substituted for the Brilliant Blue R.
Figure 2:
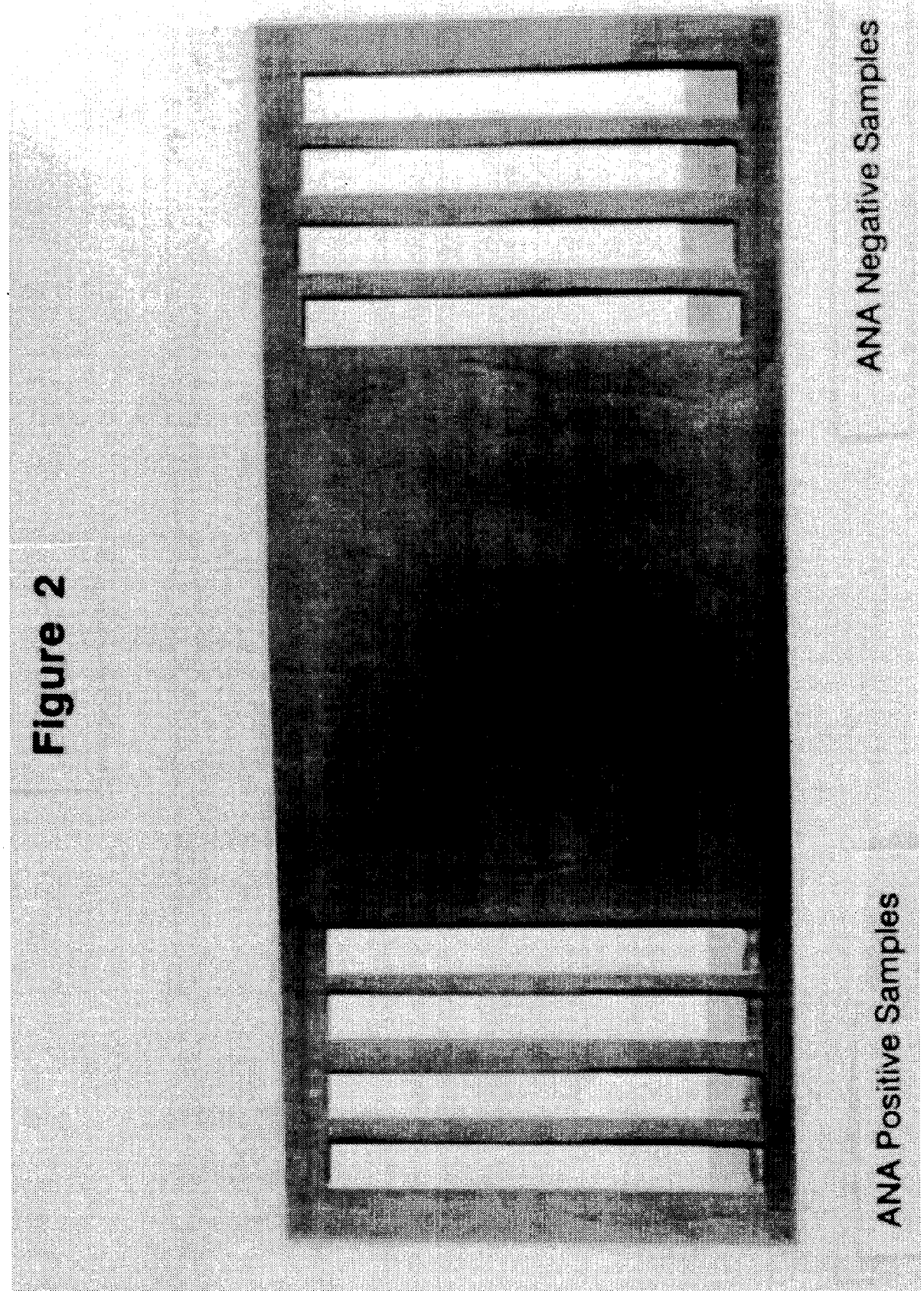
FIG. 2 pictorially depicts the results of an agglutination assay for anti-nuclear antibody (ANA) using two colloidal dyes, Brilliant Blue R and Rhodamine B. The assay was performed according to the procedures described in Example 3.

As noted above, the present invention is directed toward agglutination methods and kits for detecting the presence or amount of a substance in a biological fluid. The disclosure of the present invention shows that the use of specially selected dyes (colloidal dyes) in association with latex particles, to which a protein or non-protein molecule is bound, permits the facile detection of particles which have agglutinated in the presence of a substance.

The methods and kits of the present invention may be in a direct or indirect test format. In a direct test format, that which is observed or measured is proportional to (i.e., directly reflective of) a substance present in a sample. Conversely, in the indirect test format, that which is observed or measured is inversely proportional to (i.e., indirectly reflective of) a substance present in a sample.

Biological fluids to be tested for the presence of a substance may be derived from in vitro or in vivo sources. In vitro sources include fluids from cell cultures. In vivo sources include mammals, such as humans. Examples of biological fluids include urine, saliva, synovial fluid, cerebrospinal fluid, sputum, whole blood, serum, plasma, or fractions thereof.

Latex particles suitable for use within the present invention include those which may be reacted with a binding partner to a substance to be detected. Such particles may additionally react with a colloidal dye. Latex types include sulfate (polystyrene), carboxyl, carboxyl modified, and amidine. Generally, latex sizes range from about 0.03 to about 1.2μ. Typically, latex sizes range from about 0.03 to about 0.5μ. Preferred latex sizes range from about 0.15 to about 0.25μ. Latex is commercially available, e.g., Morton International (Chicago, Ill.), Seradyn (Indianapolis, Ind.), Interfacial Dynamics Corp. (Portland, Oreg.), Bangs Laboratories (Carmel, Ind.), Polymer Labs Ltd. (Church Stretton, United Kingdom), and Duke Scientific (Palo Alto, Calif.). It will be evident to those of ordinary skill in the art that other molecules may be substituted for latex particles.

A binding partner to a substance is a molecule which is capable of specifically binding (i.e., with a binding affinity of generally about $10^6$ liters per mole or higher) the substance. Binding partners, like substances to be detected, may be protein or non-protein in nature. Examples of binding partners include immunological binding partners (such as antibodies and antigens) and receptor-ligand binding partners (such as hormones and hormone receptors). If a substance of interest is an antigen, the binding partner used may be an antibody, and vice versa. A binding partner may be an intact molecule, a functional equivalent thereof, or a fragment of either. A binding partner may be isolated from a natural source, prepared synthetically, or genetically engineered.

Antibodies may be polyclonal or monoclonal antibodies (MAbs). Briefly, polyclonal antibodies may be produced by immunization of an animal and subsequent collection of its sera. Immunization is accomplished, for example, by systemic administration, such as by subcutaneous, intradermal or intramuscular injection, into a rabbit, rat or mouse. It is generally preferred to follow the initial immunization with one or more booster immunizations prior to sera collection. Such methodology is well known and described in a number of references. MAbs may be generally produced by the method of Kohler and Milstein (*Nature* 256:495–497, 1975; *Eur. J. Immunol.* 6:511–519, 1976). Briefly, cells of lymph nodes and/or spleens of an animal immunized with a substance are fused with myeloma cells to form hybrid cell lines ("hybridomas" or "clones"). Each hybridoma secretes a single type of immunoglobulin specific for the substance, and, like the myeloma cells, has the potential for indefinite cell division. Suitable MAbs include those of murine or human origin, or chimetic antibodies such as those which combine portions of both human and murine antibodies (i.e., antigen binding region of murine antibody plus constant regions of human antibody). Human and chimetic antibodies may be produced using methods well known by those skilled in the art. An alternative to the production of MAbs via hybridomas is the creation of MAb expression libraries using bacteriophage and bacteria (e.g., Sastry et al., *Proc. Natl. Acad. Sci. U.S.A.* 86:5728–5732, 1989; Huse et al., *Science* 246:1275–1281, 1989). In addition, numerous polyclonal and monoclonal antibodies are commercially available, e.g., Becton-Dickinson Immunocytometry Systems (San Jose, Calif.), Ortho Diagnostic System Inc. (Raritan, N.J.), and American Type Culture Collection (Rockville, Md.).

Binding of a binding partner (or of a substance itself in an indirect assay) to latex particles may be by covalent bonds or by noncovalent interactions, such as hydrophobic or electrostatic interactions. Covalent binding may be either direct or indirect, e.g., via a linker group. A direct reaction is possible when each reactant possesses a substituent capable of reacting with the other. For example, a nucleophilic group, such as an amino or sulfhydryl group, on one reactant may be capable of reacting with a carbonyl-containing group (such as an anhydride or an acyl halide) or with an alkyl group containing a good leaving group (e.g., halide) on the other. Alternatively, it may be desirable to covalently couple via a linker group. A linker group can serve to increase the chemical reactivity of a substituent, and thus increase the coupling efficiency. An increase in chemical reactivity may also facilitate the use of functional groups on molecules which would not otherwise be possible. For example, a carboxyl group may be activated. Activation of a carboxyl group includes formation of an "active ester," such as a succinimidyl ester. The term "active ester" is known to refer to esters which are highly reactive in nucleophilic substitution reactions. It will be evident to one skilled in the art that a variety of bifunctional reagents, both homo- and hetero-bifunctional (such as those described in the Pierce Chemical Co. catalog, Rockville, Ill.), may be employed as the linker group. Coupling may be effected through amino groups, carboxyl groups, sulfhydryl groups or oxidized carbohydrate residues. There are numerous references describing such methodology, e.g., U.S. Pat. No. 4,671,958 to Rodwell et al. (hereby incorporated by reference in its entirety).

As noted above, in addition to biological fluids and latex particles to which a binding partner (or a substance itself in an indirect assay) is bound, the assays and kits of the present invention employ at least one colloidal dye. Examples of colloidal dyes include Brilliant Blue R, Brilliant Green, Crystal Violet, Rhodamine B, Brilliant Cresol Black, Methyl Yellow (p-dimethylaminoazobenzene), Safranin O, Palanil® Dark Blue 3RT, Palanil® Brilliant Blue BGF, Dianix® Blue FBLN 200, and Dianix® Brilliant Yellow H10GF. Colloidal dyes are commercially available, e.g., Sigma Chemical Co. (St. Louis, Mo.). Typically, colloidal dyes are more soluble in a solvent such as methanol than in water alone. Colloidal dyes suitable for use within the present invention include those which are capable of binding to latex particles, to binding partners on latex particles, or to both, as well as those which bind to neither. In a preferred embodiment, a binding partner is reacted with latex particles prior to exposure to a colloidal dye. Mixing of a colloidal dye with latex particles to which a binding partner is bound may result in the dye being attached directly (e.g., adsorbed) to the latex and/or it may also be attached indirectly to the latex via interaction with the binding partner. The remainder of the colloidal dye remains unattached in the solution, e.g., as a fine colloidal suspension. The mixture of latex particles and suspension of colloidal dye is used. The disclosure of the present invention shows that the use of the mixture enhances the amount of colloidal dye associated with agglutinated particles. All of the methods and kits of the present invention include a mixture of latex particles (to which a substance or a binding partner is bound) and a colloidal dye suspension.

In a direct assay format of the present invention, a biological fluid sample suspected of containing a substance of interest is incubated with a suspension of colloidal dye and latex particles to which is bound a binding partner to the substance and to which the colloidal dye is attached directly or indirectly or both. Alternatively, the colloidal dye is not attached to the latex particles either directly or indirectly. Incubation of a reaction mixture comprising a biological fluid, a suspension of colloidal dye and latex particles (previously reacted with a binding partner, or with a binding partner and the colloidal dye) takes place under conditions and for a time sufficient to permit a substance of interest in the biological fluid to bind to its binding partner on the latex particles. Generally, the binding reaction is virtually instantaneous. Typically, an incubation period of about 10–15 seconds is usually more than adequate. It will be evident to those of ordinary skill in the art that some binding reactions may require extended incubation periods. Latex particles binding a substance of interest will agglutinate, i.e., particles will associate with one another via the substance and binding partner interaction. Thus, where a substance of interest is present, at least some of the latex particles will agglutinate. As a result of the agglutination, at least some unattached colloidal dye within the dye suspension is entrapped by the agglutinated particles. Further, during the separation step described below, additional unattached colloidal dye within the dye suspension may be entrapped by the agglutinated particles as a result of the separation process.

Following the incubation step, a reaction mixture is exposed to a microporous pad. Suitable microporous pads are those which permit differential migration of non-agglutinated latex particles and agglutinated latex particles. Differential migration results in substantial separation of agglutinated and non-agglutinated particles. Due to the larger size of agglutinated particles versus non-agglutinated particles, migration of agglutinated particles on a microporous pad will typically be retarded relative to non-agglutinated particles. Alternatively, a pad may be used which results in faster migration of the agglutinated particles. Examples of suitable microporous pads include fiberglass, glass fiberpaper, cellulose, and nylon. Microporous pads are commercially available, e.g., Whatman Specialty Products (Fairfield, N.J.), Gelman Sciences Inc. (Ann Arbor, Mich.), Schleicher and Schuell (Keene, N.H.), and Ahlstrom Filtration (Mt. Holly Springs, Pa.). Generally, pore sizes range from about 0.7 to about 40µ. Typically, pore sizes range from about 1 to about 6µ.

A reaction mixture is contacted with a suitable microporous pad under conditions and for a time sufficient to permit differential migration of agglutinated and non-agglutinated particles. Generally, such separation is complete within about 15–30 seconds. It will be evident to those of ordinary skill in the art that the time may be extended where appropriate. In a preferred embodiment, a microporous pad is attached to a dipstick which is placed in the reaction mixture solution. Briefly, a suitable dipstick may be constructed by attaching a microporous pad to a solid support, such as polystyrene, which can function as a dipstick. A pad may be attached to a dipstick in a variety of ways, including by use of adhesive transfer tape. Typically, a dipstick is left in the solution until the liquid reaches the top of the pad. In a particularly preferred embodiment, the microporous pad is fiberglass, attached to a dipstick. After the liquid has reached the top of the pad, the non-agglutinated particles will typically have migrated toward the top and the agglutinated particles will reside near the bottom of the pad.

Following separation of the agglutinated and non-agglutinated particles, the presence or amount of the colloidal dye associated with the agglutinated particles is detected. Ways by which a colloidal dye may be associated with agglutinated particles include direct attachment to the particles, indirect attachment to the particles, or entrapment by the particles (prior to or during separation on a microporous pad), or combinations thereof. The presence of dye associated with the agglutinated particles may be determined visually or the amount quantified, e.g., spectrophotometrically, by reflectance or densitometer scanning. A simple reflectometer may be used for a rapid quantitative-type test. Where a substance of interest is not present in a sample, no recognition of substance and binding partner will occur and, thus, no agglutination of the particles. Therefore, the dye will reside with non-agglutinated particles. Conversely, the presence of dye associated with agglutinated particles is indicative that a substance of interest is present in the sample. This substance reacted with its binding partner on the latex particles, which resulted in agglutinated particles. When more substance is present, the amount of agglutinated particles will be more concentrated and, thus, the band of color will be narrower and more intense. For illustrative purposes, it is assumed that the particles are separated on a pad whereby migration of agglutinated particles is retarded relative to non-agglutinated particles. For example, where a blue colloidal dye is used, the presence of a substance of interest is detected by the presence of concentrated blue color near the bottom of the pad. In addition, there is substantially no blue color toward the top of the pad. It may be desirable to perform assays with controls (i.e., samples in which the substance of interest is or is not present) in order to verify that the direct assay is functioning properly.

In another embodiment of a direct agglutination assay, the presence or amount of a bladder tumor analyte associated with transitional cell carcinoma (hereinafter referred to as "analyte") may be detected. Analyte is a complex derived from basal lamina, consisting of basement membrane constituent molecules or portions thereof, which has an affinity for latex particles. Analyte causes latex particles to agglutinate in its presence. Binding of substances other than analyte is eliminated by the use of latex particles modified with blocking proteins. "Blocking proteins" are those which may be used to generally block or mask sites on the latex particles which, if not blocked/masked, will nonspecifically bind substances in biological fluids. Examples of blocking proteins include serum albumins. Two or more blocking proteins may be used in combination. A biological fluid, such as urine or serum, suspected of containing the analyte is incubated with a suspension of colloidal dye and latex particles to which is bound a blocking protein and to which the colloidal dye is attached (directly or indirectly or both), to form a reaction mixture. Alternatively, the colloidal dye is not directly or indirectly attached to the latex particles. Latex particles binding analyte will agglutinate. Thus, where analyte is present, at least some of the latex particles will agglutinate. As a result of the agglutination, at least some unattached colloidal dye within the dye suspension is entrapped by the agglutinated particles. Following incubation of the reaction mixture, it is exposed to a microporous pad which permits differential migration of non-agglutinated and agglutinated latex particles. The determination of the presence or amount of analyte is based upon detection of the presence or amount of colloidal dye associated with agglutinated latex particles. The presence of dye associated with agglutinated particles is indicative that an analyte is present in the sample and reacted with the treated latex particles to yield agglutinated particles.

A number of test kit arrangements may be utilized in order to conduct direct agglutination assays. When determining the presence or amount of a substance, the kit comprises: (a) a suspension of colloidal dye and latex particles to which is bound a binding partner to a substance to be detected and, optionally, to which the colloidal dye is directly or indirectly attached or both; and (b) a microporous pad which permits differential migration of agglutinated latex particles and non-agglutinated latex particles. When determining the presence or amount of analyte, the kit comprises: (a) a suspension of colloidal dye and latex particles to which is bound a blocking protein and, optionally, to which the colloidal dye is directly or indirectly attached or both; and (b) a microporous pad which permits differential migration of agglutinated latex particles and non-agglutinated latex particles. Additional components for these kits and any of the other kits of the present invention include: positive controls and/or negative controls (e.g., to verify that the assay is functioning properly); microporous pad holders or tubes to mix latex particles with a test sample; pipet and/or disposable tips to dispense sample and reagents; test interpretation guide; and an instruction insert.

As noted above, the methods and kits of the present invention may also be in an indirect test format. In an indirect (e.g., competitive) format, a biological fluid suspected of containing a substance of interest is first incubated with a binding partner to the substance. Incubation is under conditions and for a time sufficient to permit a substance of interest in the biological fluid to bind to a binding partner, and yields a first reaction mixture. Generally, this binding reaction is virtually instantaneous. Typically, an incubation period of about 10–15 seconds is usually more than adequate. It will be evident to those of ordinary skill in the art that some binding reactions may require extended incubation periods. A first reaction mixture is then incubated with a suspension of colloidal dye and latex particles to which is bound the substance of interest and to which the colloidal dye is attached, directly or indirectly or both. Alternatively, the colloidal dye is not directly or indirectly attached to the latex particles. Incubation is under conditions and for a time sufficient to permit a binding partner which is unbound in the first reaction mixture to bind to the substance on the latex particles, thereby yielding a second reaction mixture. Generally, the binding reaction is virtually instantaneous. Typically, an incubation period of about 10–15 seconds is usually more than adequate. It will be evident to those of ordinary skill in the art that some binding reactions may require extended incubation periods. Latex particles having the substance bound thereto which bind the binding partner will agglutinate. As a result of the agglutination, at least some unattached colloidal dye within the dye suspension is entrapped by the agglutinated particles. Following the second incubation step, the second reaction mixture is then exposed to a microporous pad which permits differential migration of non-agglutinated latex particles and agglutinated latex particles. The second reaction mixture is contacted with a microporous pad under conditions and for a time sufficient to permit substantial separation of agglutinated and non-agglutinated particles. Generally, such separation is complete within about 15–30 seconds.

Following substantial separation of agglutinated and non-agglutinated particles, the presence or amount of the colloidal dye associated with the agglutinated particles is detected. Where a substance of interest is not present in a sample, the binding partner added to the sample in the first incubation will be available in the second incubation to bind the substance bound to the latex particles and agglutination of the particles will occur. Therefore, where a substance is absent from a sample, the colloidal dye will reside with agglutinated particles (i.e., the opposite of a direct format). Conversely, where a substance of interest is present in a sample, it will bind to the binding partner added to the sample. The binding partner will then not be as available to bind to the substance bound to the latex particles, and substantially no agglutination of the particles will occur. Therefore, where a substance is present in a sample, the colloidal dye will reside with non-agglutinated particles (i.e., the opposite of a direct format). For example, where a blue colloidal dye is used, the presence of a substance of interest is detected by the absence of concentrated blue color near the bottom of the pad. Conversely, the presence of concentrated blue color near the bottom of the pad is indicative of the absence of a substance of interest. It may be desirable to run controls, in which the substance of interest is and is not present, in order to verify that the indirect assay is functioning properly.

In another embodiment of an indirect agglutination assay, the presence or amount of analyte may be determined. A biological fluid, such as urine or serum, suspected of containing the analyte is incubated with a binding partner to the analyte to form a first reaction mixture. A second reaction mixture is formed by incubating the first reaction mixture with a suspension of colloidal dye and latex particles to which the analyte is bound and to which the colloidal dye is directly or indirectly attached or both. Alternatively, the colloidal dye is not directly or indirectly attached to the latex particles. Latex particles having the analyte bound thereto which bind the binding partner will agglutinate. As a result of the agglutination, at least some unattached colloidal dye within the dye suspension is entrapped by the agglutinated particles. The second reaction mixture is then exposed to a microporous pad which permits differential migration of non-agglutinated latex particles and agglutinated latex particles. The detection of the presence or amount of analyte is based upon determination of the presence or amount of colloidal dye associated with agglutinated latex particles. The presence of dye associated with the agglutinated particles is indicative that an analyte is not present in the sample as the binding partner was available to react with the treated latex particles to yield agglutinated particles.

A number of test kit arrangements may be utilized in order to conduct indirect agglutination assays. When determining the presence or amount of a substance, the kit comprises: (a) a binding partner to the substance; (b) a suspension of colloidal dye and latex particles to which is bound the substance and, optionally, to which the colloidal dye is directly or indirectly attached or both; and (c) a microporous pad which permits differential migration of agglutinated latex particles and non-agglutinated latex particles. When determining the presence or amount of the analyte, the kit comprises: (a) a binding partner to the analyte; (b) a suspension of colloidal dye and latex particles to which is bound the analyte and, optionally, to which the colloidal dye is directly or indirectly attached or both; and (c) a microporous pad which permits differential migration of agglutinated latex particles and non-agglutinated latex particles.

In another aspect of the present invention, direct and indirect assay methods and kits are provided in which two colloidal dyes are utilized. One colloidal dye is attached to latex particles only (i.e., to latex particles without a substance or a binding partner) and functions as a background-enhancing dye. Alternatively, a non-water-soluble dye (such as methyl yellow) may be attached to latex particles only and function as the background-enhancing dye. A second colloidal dye is present as a suspension and is also attached, directly or indirectly or both, to latex particles to which is bound either a substance (for an indirect assay) or a binding partner to a substance (for a direct assay). Alternatively, the second colloidal dye is not directly, or indirectly attached to the latex particles. The first and second colloidal dyes are contrasting in color. Within the context of the present invention, "contrasting" colors are meant to encompass any two colors distinguishable visually or with instrumentation. Examples of suitable pairs of colloidal dyes include Brilliant Blue R-Methyl Yellow; Brilliant Blue R-Rhodamine B; Brilliant Blue R-Safranin O; Crystal Violet-Methyl Yellow; Crystal Violet-Rhodamine B; Crystal Violet-Safranin O; Rhodamine B Brilliant Black; Brilliant Cresol Blue-Rhodamine B; Brilliant Green-Methyl Yellow; and Safranin O-Brilliant Black. The above-detailed discussions of terms and conditions for the first aspect of the present invention are hereby incorporated, where applicable, in this aspect and the remaining aspects described below.

In a direct assay format for this aspect of the present invention, a biological fluid suspected of containing a substance of interest is incubated with latex particles to which a first colloidal dye is directly or indirectly attached and a suspension of second colloidal dye and latex particles having a binding partner to the substance bound thereto and to which the second colloidal dye is directly or indirectly attached or both. Alternatively, the second colloidal dye is not directly or indirectly attached to the latex particles. Incubation is under conditions and for a time sufficient to permit a substance of interest in the biological fluid to bind to its binding partner on the latex particles. Latex particles binding a substance of interest will agglutinate. Thus, where a substance of interest is present, at least some of the latex particles will agglutinate. As a result of the agglutination, at least some unattached second colloidal dye within the dye suspension is entrapped by the agglutinated particles. Following the incubation step, the reaction mixture is exposed to a microporous pad which permits differential migration of non-agglutinated latex particles and agglutinated latex particles. The reaction mixture is contacted with a microporous pad under conditions and for a time sufficient to permit substantial separation of agglutinated and non-agglutinated particles.

Following substantial separation of agglutinated and non-agglutinated particles, the presence or amount of the second colloidal dye associated with the agglutinated particles is detected. Where a substance of interest is not present in a sample, there will be no binding of the substance to its binding partner and, thus, no agglutination of the particles. Therefore, the first and second dyes will reside with non-agglutinated particles. Conversely, the presence of the second dye associated with agglutinated particles is indicative that a substance of interest is present in the sample. This substance reacted with its binding partner on the latex particles having the second dye attached, which resulted in agglutinated particles. For example, where a first colloidal dye is red and a second colloidal dye is blue, the presence of a substance of interest is detected by the presence of concentrated blue color near the bottom of the pad and red color above the blue color. In the absence of a substance of interest, both the latex particles with a red colloidal dye and the latex particles with a blue colloidal dye will be non-agglutinated and both will migrate up the pad to generally yield a single combined color (purple) throughout the pad.

In another embodiment of a direct agglutination assay for this aspect of the present invention, the presence or amount of analyte within a biological fluid may be determined. A biological fluid, such as urine or serum, suspected of containing analyte is incubated with latex particles to which a first colloidal dye is directly or indirectly attached and a suspension of second colloidal dye and latex particles to which a blocking protein is bound and to which the second colloidal dye is attached. The second colloidal dye is contrasting in color to the first colloidal dye. Alternatively, the second colloidal dye is not directly or indirectly attached to the latex particles. Latex particles binding analyte will agglutinate. Thus, where analyte is present, at least some of the latex particles will agglutinate. As a result of the agglutination, at least some unattached second colloidal dye within the dye suspension is entrapped by the agglutinated particles. Following incubation, the reaction mixture is exposed to a microporous pad which permits differential migration of non-agglutinated and agglutinated latex particles. The determination of the presence or amount of analyte is based upon detection of the presence or amount of the second colloidal dye associated with agglutinated latex particles. The presence of the second dye associated with agglutinated particles is indicative that an analyte is present in the sample and reacted with the latex particles treated with blocking protein to yield agglutinated particles.

A number of test kit arrangements may be utilized in order to conduct direct agglutination assays. When determining the presence or amount of a substance, the kit comprises: (a) latex particles to which are attached a first colloidal dye; (b) a suspension of second colloidal dye and latex particles to which is bound a binding partner to a substance to be detected and, optionally, to which the second colloidal dye, that is contrasting in color to the first colloidal dye, is directly or indirectly attached or both; and (c) a microporous pad which permits differential migration of agglutinated latex particles and non-agglutinated latex particles. Kit components (a), (b), and (c) may be present in separate containers, or component (a) may be combined with (b). When determining the presence or amount of analyte, the kit comprises: (a) latex particles to which are attached a first colloidal dye; (b) a suspension of second colloidal dye and latex particles to which is bound a blocking protein and, optionally, to which the second colloidal dye, that is contrasting in color to the first colloidal dye, is directly or indirectly attached or both; and (c) a microporous pad which permits differential migration of agglutinated latex particles and non-agglutinated latex particles. Kit components (a), (b), and (c) may be present in separate containers, or component (a) may be combined with (b).

The methods and kits of this aspect of the present invention may also be in an indirect test format. A biological fluid suspected of containing a substance of interest is first incubated with a binding partner to the substance. Incubation is under conditions and for a time sufficient to permit the substance of interest in the biological fluid to bind to a binding partner, and yields a first reaction mixture. A second reaction mixture is formed by incubation of a first reaction mixture with latex particles to which a first colloidal dye are attached and a suspension of second colloidal dye and latex particles to which the substance of interest is bound and to which the second colloidal dye is attached that is contrasting in color to the first colloidal dye. Alternatively, the second colloidal dye is not directly or indirectly attached to the latex particles. Incubation is under conditions and for a time sufficient to permit a binding partner which is unbound in the first reaction mixture to bind to the substance on the latex particles. Latex particles having the substance bound thereto which bind the binding partner will agglutinate. As a result of the agglutination, at least some unattached second colloidal dye within the dye suspension is entrapped by the agglutinated particles. The second reaction mixture is then exposed to a microporous pad which permits differential migration of non-agglutinated latex particles and agglutinated latex particles.

Following substantial separation of agglutinated and non-agglutinated particles, the presence or amount of the second colloidal dye associated with the agglutinated particles is detected. Where a substance of interest is not present in a sample, the binding partner added to the sample will be available to bind to the substance bound to the latex particles and agglutination of these particles will occur. Therefore, where a substance is absent from a sample, the second colloidal dye will reside with agglutinated particles. Conversely, where a substance of interest is present in the sample, it will bind to the binding partner added to the sample. The binding partner will then not be as available to bind to the substance bound to the latex particles and substantially no agglutination of these particles will occur. Therefore, where a substance is present in a sample, the second colloidal dye will reside with non-agglutinated particles. For example, where a first colloidal dye is red and a second colloidal dye is blue, the presence of a substance of interest is detected by the presence of a single color (purple) which is the combination of the red and blue colors. Conversely, the presence of concentrated blue color near the bottom of the pad and red color near the top of the pad is indicative of the absence of a substance of interest.

In another embodiment of an indirect agglutination assay of this aspect of the present invention, the presence or amount of analyte may be determined. A biological fluid, such as urine or serum, suspected of containing analyte is first incubated with a binding partner to the analyte to yield a first reaction mixture. A second reaction mixture is formed by incubation of the first reaction mixture with latex particles to which a first colloidal dye is attached and a suspension of second colloidal dye and latex particles to which the analyte is bound and to which the second colloidal dye is attached. The second colloidal dye is contrasting in color to the first colloidal dye. Alternatively, the second colloidal dye is not directly or indirectly attached to the latex particles. Latex particles having the analyte bound thereto which bind the binding partner will agglutinate. As a result of the agglutination, at least some unattached second colloidal dye within the dye suspension is entrapped by the agglutinated particles. The second reaction mixture is then exposed to a microporous pad which permits differential migration of non-agglutinated latex particles and agglutinated latex particles. Following substantial separation of agglutinated and non-agglutinated particles, the presence or amount of the second colloidal dye associated with the agglutinated particles is detected. Where an analyte is absent from a sample, the second colloidal dye will reside with agglutinated particles. Conversely, where an analyte is present in a sample, the second colloidal dye will reside with non-agglutinated particles.

A number of test kit arrangements may be utilized in order to conduct indirect agglutination assays. When determining the presence or amount of a substance, the kit comprises: (a) a binding partner to the substance; (b) latex particles to which are attached a first colloidal dye; (c) a suspension of second colloidal dye and latex particles to which is bound the substance and, optionally, to which the second colloidal dye, that is contrasting in color to the first colloidal dye, is directly or indirectly attached or both; and (d) a microporous pad which permits differential migration of agglutinated latex particles and non-agglutinated latex particles. Kit components (a), (b), (c), and (d) may be in separate containers, or component (b) may be combined with (c). When determining the presence or amount of analyte in a biological fluid, the kit comprises: (a) a binding partner to the analyte; (b) latex particles to which are attached a first colloidal dye; (c) a suspension of second colloidal dye and latex particles to which is bound the analyte and, optionally, to which the second colloidal dye, that is contrasting in color to the first colloidal dye, is directly or indirectly attached or both; and (d) a microporous pad which permits differential migration of agglutinated latex particles and non-agglutinated latex particles. Kit components (a), (b), (c), and (d) may be in separate containers, or component (b) may be combined with (c).

In another aspect of the present invention, direct and indirect assay methods and kits are provided which utilize a colloidal dye and a non-water-soluble dye. A colloidal dye is present as a suspension and is also attached directly or indirectly or both to latex particles to which is bound either a substance (for an indirect assay) or a binding partner to a substance (for a direct assay). Alternatively, the colloidal dye is not directly or indirectly attached to the latex particles. A non-water-soluble dye is attached (e.g., adsorbed, absorbed, or covalently linked) to a microporous pad and functions as a background-enhancing dye. Examples of non-water-soluble dyes include methyl yellow, sudan III, fast garnet, and Dianix® brilliant yellow H10GF. A colloidal dye and a background-enhancing dye are "contrasting" in color.

In a direct assay format of this aspect of the present invention, a biological fluid suspected of containing a substance of interest is incubated with a suspension of colloidal dye and latex particles to which a binding partner to the substance is bound and to which the colloidal dye is attached. Alternatively, the colloidal dye is not directly or indirectly attached to the latex particles. Incubation of the reaction mixture is under conditions and for a time sufficient to permit a substance of interest and the biological fluid to bind to its binding partner on the latex particles. Latex particles binding a substance of interest will agglutinate. Thus, where a substance of interest is present, at least some of the latex particles will agglutinate. As a result of the agglutination, at least some unattached colloidal dye within the dye suspension is entrapped by the agglutinated particles. Following the incubation step, the reaction mixture is exposed to a microporous pad to which is attached a non-water-soluble background-enhancing dye that is contrasting in color to the colloidal dye. For example, briefly, a microporous pad with background-enhancing dye may be prepared by immersion of a pad in a solution of a background-enhancing dye. The pad is removed and permitted to dry. The microporous pad permits differential migration of non-agglutinated latex particles and agglutinated latex particles. The reaction mixture is contacted with a microporous pad under conditions and for a time sufficient to permit substantial separation of agglutinated and non-agglutinated particles.

Following substantial separation of agglutinated and non-agglutinated particles, the presence or amount of the colloidal dye associated with the agglutinated particles is detected. Where a substance of interest is not present in a sample, no recognition of substance and binding partner will occur and, thus, no agglutination of the particles. Therefore, the colloidal dye will reside with non-agglutinated particles. Conversely, the presence of colloidal dye associated with agglutinated particles is indicative that a substance of interest is present in the sample. This substance reacted with its binding partner on the latex particles, which resulted in agglutinated particles. Regardless of whether a substance of interest is present, the non-water-soluble background-enhancing dye does not migrate on the pad. However, the colloidal dye associated with agglutinated particles will override the background-enhancing dye on the portion of the pad where the agglutinated particles reside after substantial separation from the non-agglutinated particles. For example, where the colloidal dye is blue and the non-water-soluble background-enhancing dye is yellow, the presence of a substance of interest is detected by the presence of concentrated blue color near the bottom of the pad and the presence of yellow color above the blue color. Where a substance of interest is absent in the sample, the combination of the colors (green) is observed on the pad.

In another embodiment of a direct agglutination assay of this aspect of the present invention, the presence or amount of analyte may be determined. A biological fluid, such as urine or serum, suspected of containing the analyte is incubated with a suspension of colloidal dye and latex particles to which a blocking protein is bound and to which the colloidal dye is attached. Alternatively, the colloidal dye is not directly or indirectly attached to the latex particles. Latex particles binding analyte will agglutinate. Thus, where analyte is present, at least some of the latex particles will agglutinate. As a result of the agglutination, at least some unattached colloidal dye within the dye suspension is entrapped by the agglutinated particles. Following incubation of the reaction mixture, it is exposed to a microporous pad to which a non-water-soluble background-enhancing dye is attached that is contrasting in color to the colloidal dye. The microporous pad permits differential migration of non-agglutinated latex particles and agglutinated latex particles. The determination of the presence or amount of analyte is based upon detection of the presence or amount of colloidal dye associated with agglutinated latex particles. The presence of dye associated with agglutinated particles is indicative that analyte is present in the sample and reacted with treated latex particles to yield agglutinated particles.

A number of test kit arrangements may be utilized in order to conduct direct agglutination assays. When determining the presence or amount of a substance, the kit comprises: (a) a suspension of colloidal dye and latex particles to which is bound a binding partner to a substance to be detected and, optionally, to which the colloidal dye is directly or indirectly attached or both; and (b) a microporous pad to which is attached a non-water-soluble background-enhancing dye, that is contrasting in color to the colloidal dye, and which permits differential migration of agglutinated latex particles and non-agglutinated latex particles. When determining the presence or amount of the analyte, the kit comprises: (a) a suspension of colloidal dye and latex particles to which is bound a blocking protein and, optionally, to which the colloidal dye is directly or indirectly attached or both; and (b) a microporous pad to which is attached a non-water-soluble background-enhancing dye, that is contrasting in color to the colloidal dye, and which permits differential migration of agglutinated latex particles and non-agglutinated particles.

The methods and kits of this aspect of the present invention may also be in an indirect test format. A biological fluid suspected of containing a substance of interest is first incubated with a binding partner to the substance. Incubation is under conditions and for a time sufficient to permit a substance of interest in the biological fluid to bind to a binding partner, thereby yielding a first reaction mixture. A second reaction mixture is formed by incubation of the first reaction mixture with a suspension of colloidal dye and latex particles to which the substance of interest is bound and to which the colloidal dye is attached. Alternatively, the colloidal dye is not directly or indirectly attached to the latex particles. Incubation is under conditions and for a time sufficient to permit a binding partner which is unbound in the first reaction mixture to bind to the substance on the latex particles. Latex particles having the substance bound thereto which bind the binding partner will agglutinate. As a result of the agglutination, at least some unattached colloidal dye within the dye suspension is entrapped by the agglutinated particles. The second reaction mixture is then exposed to a microporous pad to which is attached a non-water-soluble background-enhancing dye that is contrasting in color to the colloidal dye. The microporous pad permits differential migration of non-agglutinated latex particles and agglutinated latex particles.

Following substantial separation of agglutinated and non-agglutinated particles, the presence or amount of colloidal dye associated with the agglutinated particles is detected. Where a substance of interest is not present in a sample, the binding partner added to the sample will be available to bind to the substance bound to the latex particles and agglutination of the particles will occur. Therefore, where a substance is absent from a sample, the colloidal dye will reside with agglutinated particles. Conversely, where a substance of interest is present in a sample, it will bind to the binding partner added to the sample. The binding partner will then not be as available to bind to the substance bound to the latex particles and substantially no agglutination of the particles will occur. Therefore, where a substance is present in a sample, the colloidal dye will reside with non-agglutinated particles. For example, where a colloidal dye is blue and a non-water-soluble background-enhancing dye is yellow, the presence of a substance of interest is detected by the presence of the combined color (green) and the absence of concentrated blue color near the bottom of the pad. Conversely, the presence of concentrated blue color near the bottom of the pad and yellow color above it is indicative of the absence of a substance of interest.

In another embodiment of an indirect agglutination assay of this aspect of the present invention, the presence or amount of analyte may be detected. A biological fluid, such as urine or serum, suspected of containing analyte is first incubated with a binding partner to the analyte to form a first reaction mixture. A second reaction mixture is formed by incubation of the first reaction mixture with a suspension of colloidal dye and latex particles to which the analyte is bound and to which the colloidal dye is attached directly or indirectly or both. Alternatively, the colloidal dye is not directly or indirectly attached to the latex particles. Latex particles having the analyte bound thereto which bind the binding partner will agglutinate. As a result of the agglutination, at least some unattached colloidal dye within the dye suspension is entrapped by the agglutinated particles. The second reaction mixture is then exposed to a microporous pad to which is attached a non-water-soluble background-enhancing dye that is contrasting in color to the colloidal dye. The microporous pad permits differential migration of non-agglutinated latex particles and agglutinated latex particles. Following substantial separation of agglutinated and non-agglutinated particles, the presence or amount of colloidal dye associated with the agglutinated particles is detected. Where an analyte is absent from a sample, the colloidal dye will reside with the agglutinated particles. Conversely, where an analyte is present in a sample, the colloidal dye will reside with non-agglutinated particles.

A number of test kit arrangements may be utilized in order to conduct indirect agglutination assays. When determining the presence or amount of a substance, the kit comprises: (a) a binding partner to the substance; (b) a suspension of colloidal dye and latex particles to which is bound the substance and, optionally, to which the colloidal dye is directly or indirectly attached or both; and (c) a microporous pad to which is attached a non-water-soluble background-enhancing dye, that is contrasting in color to the colloidal dye, and which permits differential migration of agglutinated latex particles and non-agglutinated latex particles. When determining the presence or amount of analyte in a biological fluid, the kit comprises: (a) a binding partner to the analyte; (b) a suspension of colloidal dye and latex particles to which is bound the analyte and, optionally, to which the colloidal dye is directly or indirectly attached or both; and (c) a microporous pad to which is attached a non-water-soluble background-enhancing dye, that is contrasting in color to the colloidal dye, and which permits differential migration of agglutinated latex particles and non-agglutinated latex particles.

In another aspect of the present invention, direct and indirect assay methods and kits are provided which utilize a colloidal dye and a water-soluble dye. The colloidal dye is present as a suspension and is also attached directly or indirectly or both to latex particles to which is bound either a substance (for an indirect assay) or a binding partner to a substance (for a direct assay). Alternatively, the colloidal dye is not directly or indirectly attached to the latex particles. The water-soluble dye does not associate with latex particles and functions as a background-enhancing dye. Examples of water-soluble dyes include Crescent® red, Crescent® blue, and Crescent® yellow. A colloidal dye and a water-soluble background-enhancing dye are "contrasting" in color.

In a direct assay format for this aspect of the present invention, a biological fluid suspected of containing a substance of interest is incubated with a water-soluble background-enhancing dye and a suspension of colloidal dye and latex particles to which a binding partner to the substance is bound and to which the colloidal dye is attached directly or indirectly or both. Alternatively, the colloidal dye is not directly or indirectly attached to the latex particles. Incubation of the reaction mixture is under conditions and for a time sufficient to permit a substance of interest in the biological fluid to bind to its binding partner on the latex particles. Latex particles binding a substance of interest will agglutinate. Thus, where a substance of interest is present, at least some of the latex particles will agglutinate. As a result of the agglutination, at least some unattached colloidal dye within the dye suspension is entrapped by the agglutinated particles. Following the incubation step, the reaction mixture is exposed to a microporous pad which permits differential migration of non-agglutinated latex particles and agglutinated latex particles. The reaction mixture is contacted with a microporous pad under conditions and for a time sufficient to permit substantial separation of agglutinated and non-agglutinated particles.

Following substantial separation of agglutinated and non-agglutinated particles, the presence or amount of colloidal dye associated with the agglutinated particles is detected. Where a substance of interest is not present in a sample, there will be no substance and binding partner reaction and, thus, no agglutination of the particles. Therefore, the colloidal dye will reside with non-agglutinated particles. Conversely, the presence of dye associated with agglutinated particles is indicative that a substance of interest is present in the sample. This substance reacted with its binding partner on latex particles, which resulted in agglutinated particles. For example, where a colloidal dye is blue and a water-soluble background-enhancing dye is yellow, the presence of a substance of interest is detected by the presence of concentrated blue color near the bottom of the pad and yellow color above the blue. In the absence of a substance of interest, the combined color (green) is observed on the pad.

In another embodiment of a direct agglutination assay of this aspect of the present invention, the presence or amount of analyte may be determined. A biological fluid, such as urine or serum, suspected of containing the analyte is incubated with a water-soluble background-enhancing dye and a suspension of colloidal dye and latex particles to which a blocking protein is bound and to which the colloidal dye is directly or indirectly attached or both. Alternatively, the colloidal dye is not directly or indirectly attached to the latex particles. Latex particles binding analyte will agglutinate. Thus, where analyte is present, at least some of the latex particles will agglutinate. As a result of the agglutination, at least some unattached colloidal dye within the dye suspension is entrapped by the agglutinated particles. Following incubation of the reaction mixture, it is exposed to a microporous pad which permits differential migration of non-agglutinated and agglutinated latex particles. The determination of the presence or amount of analyte is based upon determination of the presence or amount of colloidal dye associated with agglutinated latex particles. The presence of dye associated with agglutinated particles is indicative that an analyte is present in the sample and reacted with the treated latex particles to yield agglutinated particles.

A number of test kit arrangements may be utilized in order to conduct direct agglutination assays. When determining the presence or amount of a substance, the kit comprises: (a) a water-soluble background-enhancing dye; (b) a suspension of colloidal dye and latex particles to which is bound a binding partner to a substance to be detected and, optionally, to which the colloidal dye, that is contrasting in color to the water-soluble background-enhancing dye, is directly or directly attached or both; and (c) a microporous pad which permits differential migration of agglutinated latex particles and non-agglutinated latex particles. Kit components (a), (b), and (c) may be present in separate containers, or component (a) may be combined with (b). When determining the presence or amount of analyte, the kit comprises: (a) a water-soluble background-enhancing dye; (b) a suspension of colloidal dye and latex particles to which is bound a blocking protein and, optionally, to which the colloidal dye, that is contrasting in color to the water-soluble background-enhancing dye, is directly or indirectly attached or both; and (c) a microporous pad which permits differential migration of agglutinated latex particles and non-agglutinated latex particles. Kit components (a), (b), and (c) may be present in separate containers, or component (a) may be combined with (b).

The methods and kits of this aspect of the present invention may also be in an indirect test format. A biological fluid suspected of containing a substance of interest is first incubated with a binding partner to the substance and a water-soluble background-enhancing dye, thereby forming a first reaction mixture. Incubation is under conditions and for a time sufficient to permit a substance of interest in the biological fluid to bind to a binding partner. A second reaction mixture is formed by incubation of the first reaction mixture with a suspension of colloidal dye and latex particles to which is bound the substance of interest is bound and to which the colloidal dye is directly or indirectly attached or both. The colloidal dye is contrasting in color to the background-enhancing dye. Alternatively, the colloidal dye is not directly or indirectly attached to the latex particles. Incubation is under conditions and for a time sufficient to permit a binding partner which is unbound in the first reaction mixture to bind to the substance on the latex particles. Latex particles having the substance bound thereto which bind the binding partner will agglutinate. As a result of the agglutination, at least some unattached colloidal dye within the dye suspension is entrapped by the agglutinated particles. The second reaction mixture is then exposed to a microporous pad which permits differential migration of non-agglutinated latex particles and agglutinated latex particles. The order of addition of a water-soluble background-enhancing dye may be varied. For example, a water-soluble background-enhancing dye may be added along with the treated latex particles to a first reaction mixture comprising a biological fluid suspected of containing a substance and a binding partner of the substance.

Following substantial separation of agglutinated and non-agglutinated particles, the presence and amount of colloidal dye associated with agglutinated particles is detected. Where a substance of interest is not present in a sample, the binding partner added to the sample will be available to bind to the substance bound to the latex particles and agglutination of the particles will occur. Therefore, where a substance is absent from a sample, the colloidal dye will reside with the agglutinated particles. Conversely, where a substance of interest is present in a sample, it will bind to the binding partner added to the sample. The binding partner will then not be as available to bind to the substance bound to the latex particles and substantially no agglutination of the particles will occur. Therefore, where a substance is present in a sample, the colloidal dye will reside with non-agglutinated particles. For example, where a colloidal dye is blue and a water-soluble background-enhancing dye is yellow, the presence of a substance of interest is detected by the presence of the combination of colors (green) generally throughout the pad. Conversely, the presence of concentrated blue color near the bottom of the pad and yellow color above the blue is indicative of the absence of a substance of interest.

In another embodiment of an indirect agglutination assay of this aspect of the present invention, the presence or amount of analyte may be determined. A biological fluid, such as urine or serum, suspected of containing the analyte is incubated with a water-soluble background-enhancing dye and a binding partner of the analyte, thereby forming a first reaction mixture. A second reaction mixture is formed by incubation of the first reaction mixture with a suspension of colloidal dye and latex particles to which the analyte is bound and to which the colloidal dye is directly or indirectly attached or both. The colloidal dye is contrasting in color to the background-enhancing dye. Alternatively, the colloidal dye is not directly or indirectly attached to the latex particles. Latex particles having the analyte bound thereto which bind the binding partner will agglutinate. As a result of the agglutination, at least some unattached colloidal dye within the dye suspension is entrapped by the agglutinated particles. The second reaction mixture is then exposed to a microporous pad which permits differential migration of non-agglutinated latex particles and agglutinated latex particles. Following substantial separation of agglutinated and non-agglutinated particles, the presence or amount of colloidal dye associated with agglutinated particles is detected. Where a substance is absent from a sample, the colloidal dye will reside with agglutinated particles. Conversely, where a substance is present in a sample, the colloidal dye will reside with non-agglutinated particles.

A number of test kit arrangements may be utilized in order to conduct indirect agglutination assays. When determining the presence or amount of a substance, the kit comprises: (a) a binding partner to the substance; (b) a water-soluble background-enhancing dye; (c) a suspension of colloidal dye and latex particles to which is bound the substance and, optionally, to which the colloidal dye, that is contrasting in color to the background-enhancing dye, is directly or indirectly attached or both; and (d) a microporous pad which permits differential migration of agglutinated latex particles and non-agglutinated latex particles. Kit components (a), (b), (c), and (d) may be present in separate containers, or component (b) may be combined with either component (a) or (c). When determining the presence or amount of analyte in a biological fluid, the kit comprises: (a) a binding partner to the analyte; (b) a water-soluble background-enhancing dye; (c) a suspension of colloidal dye and latex particles to which is bound the analyte and, optionally, to which the colloidal dye, that is contrasting in color to the background-enhancing dye, is directly or indirectly attached or both; and (d) a microporous pad which permits differential migration of agglutinated latex particles and non-agglutinated particles. Kit components (a), (b), (c), and (d) may be present in separate containers, or component (b) may be combined with either component (a) or (c).

The follow examples are offered by way of illustration and not by way of limitation.

EXAMPLES

EXAMPLE 1

A Quantitative RF Assay Read by Densitometry

The RF assay described below is a latex agglutination test for the detection of Rheumatoid Factors in human serum. It was observed in 1931 that there was a common factor in serum relating to rheumatoid arthritis. It was later demonstrated that sheep cells coated with human gamma globulin would agglutinate when mixed with serum from many patients with rheumatoid arthritis.

Rheumatoid Factor (RF) is a group of antibodies that react with both human and animal IgG. Approximately 70%–80% of patients with human RF present on their serum have rheumatoid arthritis. It is an inflammatory condition involving connective tissue structures and synovial joints resulting in pain and swelling in the joints. Studies have indicated that the severity of rheumatoid arthritis is associated with increasing levels of RF.

The RF reagent consists of latex particles coated with human gamma globulin and a colloidal dye. If the RF is present at a significant level and is mixed with the RF reagent, it will combine with the latex particles to produce an agglutination reaction which results in a visual color change by separation.

An RF latex reagent with no background-enhancing dye was prepared as follows. A stock latex reagent was made by adding 5 mg of Human Gamma Globulin II, III (Sigma Chemical) to 100 ml of latex suspension Lytron 5251 or 601 (Morton International). The latex suspension was mixed for 1 hour and placed in a water bath for 1 hour at 56° C. The stock suspension was then mixed on a magnetic stirrer for 18–24 hours at room temperature. Brilliant Blue R dye (0.5 gm) was added to the latex suspension and mixed for 1 hour.

An RF working latex reagent was prepared by adding 4 ml of the RF stock reagent to 1 liter of 0.13M glycine buffer, pH 8.2, containing 20 mg of BSA (Sigma) and 0.1% sodium azide as a preservative. The working reagent was stored at 2° C.–8° C. until used.

A dipstick was prepared from the following materials: polystyrene sheets 0.014 to 0.025 mil (Laminations Supplies, Seattle, Wash.); Scott adhesive tape 0.02 mil 1 inch #Y-9485PC (3M Company, St. Paul, Minn.); microporous pad material Ahlstrom #161 (Ahlstrom Filtration, Inc., Mt. Holly Springs, Pa.); and Scott white vinyl tape 1 inch width #471 (3M Company, St. Paul, Minn.). The dipstick is constructed by placing a 1×7.5 inch strip of adhesive transfer tape (3M #Y-9485PC) aligned along the lower edge of a 0.018 mil polystyrene sheet 3.75×7.5 inches. A strip of 1×7.5 inch microporous pad material (Ahlstrom #161) was placed directly on top of the transfer tape. The microporous pad strip was pressed firmly to the transfer tape for a uniform adhesion. A strip of white vinyl tape 1×7.5 inch (3M #471) was placed over the microporous pad leaving 8 mm at the bottom exposed and thus overlapping the pad 8 mm on the polystyrene sheet. At the top of the polystyrene sheet (the opposite end of the exposed microporous pad), a score or cut approximately 0.007 mm was made 0.5 inch from the top. This is to allow the dipsticks to remain in a pod and then be broken off when needed. The polystyrene sheet is then cut into 0.25 in strips allowing 0.125 to 0.25 uncut at the top to allow the strips to remain in a pod. Each pod contains strips.

An RF positive serum with a titer of 1:2560 was serial diluted from 1:20 to 1:20,480. Each dilution was tested with the RF reagent without background-enhancing dye by the following. Into each 12×75 mm plastic tube, 65 µof RF working latex reagent was added. Five µl of sample or control was added to each tube containing the reagent and all tubes were shaken for 10 seconds. A dipstick was placed in each tube and read after 15 seconds.

A densitometric reading was taken, using a Zenith video densitometer, by scanning the length of the dipstick, and the peak height was recorded. The readings demonstrated a dilution curve relating peak height (arbitrary units) to the sample dilution (Table I).

TABLE I

| PEAK HEIGHT DENSITOMETER READINGS OF RF POSITIVE SERUMS | |
|---|---|
| DILUTION OF RF | PEAK HEIGHT IN DENSITOMETER (ARBITRARY UNITS) |
| 1:20 | 117 |
| 1:40 | 119 |
| 1:80 | 131 |
| 1:160 | 129 |
| 1:320 | 122 |
| 1:640 | 78 |
| 1:1280 | 73 |
| 1:2560 | 75 |
| 1:5120 | 62 |
| 1:10240 | 55 |
| 1:20480 | 35 |

EXAMPLE 2

RF Assay Using Two Colloidal Dyes

An RF reagent was prepared by adding 5 mg/dl of human gamma globulin to 100 ml of Lytron 601 latex 40% stock suspension, pH 7.8, mixing for 1 hour, heating at 56° C. for 1 hour, and mixing at room temperature for 18 to 24 hours. To the 10 ml of IgG bonded latex suspension, 50 mg of Brilliant Blue R dye (Sigma Chemical, St. Louis, Mo.) was added and mixed for 1 hour. To a second 10 ml aliquot of Lytron 601 latex 40%, pH 7.8, suspension, 50 mg of Safranin O (Sigma Chemical) was added and mixed for 1 hour.

The stock RF latex containing Brilliant Blue R was diluted by adding 400 µl of the latex to 100 ml of 0.1M glycine buffer, pH 8.2, containing 20 mg/L BSA. The non-IgG bound latex suspension containing Safranin O dye was diluted by adding 400 µl of latex to 100 ml of 0.1M glycine buffer containing 500 mg/L BSA. The non-IgG bound diluted latex suspension was then mixed for 1 hour and heated in a water bath for 8 hours at 56° C.

An RF working reagent was prepared by adding 100 ml of the Brilliant Blue R latex suspension to 100 ml of Safranin O latex suspension and mixed for 1 hour.

The RF working reagent was tested with positive and negative RF sera, by adding 65 μl of latex reagent to each 12×75 mm tube and 5 μl of serum sample to each tube. The tube was mixed and a dipstick placed in each tube. A positive test demonstrated separation of dyes and dyed latex particles with the blue remaining at the bottom and the red migrating to the top of the pad. A negative test revealed an even purple (red+blue) color throughout the dipstick pad.

Four serum samples from a normal population and four serum samples that were confirmed RF positive were tested using the RF dipstick working reagent. The four normal serums demonstrated negative results and the four RF positive serums demonstrated positive results.

EXAMPLE 3

An Ana Latex Assay Using Two Colloidal Dyes

The detection of antibodies to nuclear antigens (ANA) is one of the commonly used test for autoantibodies. Although the ANA test can be useful in aiding in the diagnosis of several autoimmune diseases, the most common use is to help rule out the diagnosis of active systemic lupus erythematosus (SLE).

An ANA reagent was prepared by adding 20 mg/dl of Nucleohistone (calf thymus, Sigma Chemical #N-8627) to 100 ml of Lytron 601 latex 40% stock suspension, pH 7.8, mixing for 18 to 24 hours at room temperature. To a 10 ml aliquot of Nucleohistone bonded latex suspension, 50 mg of Brilliant Blue R dye (Sigma Chemical, St. Louis, Mo., B-0149) was added and mixed for 1 hour. To a 10 ml aliquot of Lytron 601 Latex 40%, pH 7.8 suspension, 50 mg of Rhodamine B Sigma Chemical #R-6626 was added and mixed for 1 hour.

The stock ANA latex containing Brilliant Blue R was diluted by adding 400 μl of the latex to 100 ml of 0.1M glycine buffer, pH 8.2, containing 20 mg/L BSA. The unbound latex suspension containing Rhodamine B dye was diluted by adding 400 μl of latex to 100 ml of 0.1M glycine buffer containing 500 mg/L BSA. The diluted latex suspension was then mixed for 1 hour and heated in a water bath for 8 hours at 56° C.

An ANA working reagent was prepared by adding 100 ml of the Brilliant Blue R dyed latex suspension to 100 ml of Rhodamine B dyed unbound latex suspension and mixed for one hour.

The ANA working reagent was tested with positive and negative ANA sera, by adding 65 μl of latex reagent to each 12×75 mm tube and 2 μl of serum sample to each tube. The tube was mixed and a dipstick was placed in each tube. A positive test demonstrated a separation of dyes and dyed latex particles with the blue remaining at the bottom and the pinkish red migrating to the top of the pad. A negative test revealed even lavender color throughout the dipstick pad.

Four serum samples from a normal population and four serum samples that were confirmed ANA positive were tested using the ANA working reagent. The four normal serums demonstrated negative results and the four ANA positive serums demonstrated positive results.

EXAMPLE 4

RF Assay With Background-Enhancing Dye on the Pad

The RF reagent was prepared using no yellow background-enhancing dye as in Example 1. Before the fiberglass was placed on the dipstick, it was immersed in a tray containing methyl yellow dye (Sigma) dissolved in methanol (40 mg/dl of methyl yellow dye). The fiberglass (Ahlstrom 161) was allowed to dry and mounted on the dipstick using the same procedure described above.

Thirty serum samples from a normal population were tested with the RF dipstick and 29 negative results demonstrated a 97% specificity. Twenty-two RF positives were tested and 20 were positive, demonstrating a 91% sensitivity.

EXAMPLE 5

RF Assay with Colloidal Dye and Water-Soluble Background-Enhancing Dye

The RF latex reagent was prepared as follows. A stock latex reagent was made by adding 5 mg of Human Gamma Globulin II, III (Sigma Chemical) to 100 ml of latex suspension Lytron 5251 or 601 (Morton International). The latex suspension was mixed for 1 hour and placed in a water bath for 1 hour at 56° C. The stock suspension was then mixed on a magnetic stirrer for 18–24 hours at room temperature. Brilliant Blue R dye (0.5 gm) was added to the latex suspension and mixed for 1 hour.

An RF working reagent was prepared by adding 4 ml of the RF stock reagent to 1 liter of 0.13M glycine buffer, pH 8.2, containing 4 ml of yellow dye (Crescent), 20 mg of BSA (Sigma) and 0.1% sodium azide as a preservative. The working reagent was stored at 2° C.–8° C. until used.

The qualitative RF dipstick procedure was performed as follows. Into each 12×75 mm plastic tube, 65 μl of RF working reagent was added. Five μl of sample or control was added to each tube containing the reagent and all tubes were shaken for 10 seconds. A dipstick was placed in each tube and read after 15 seconds. The RF dipstick procedure was tested using 100 serum samples from a normal population, two were found to be positive and confirmed by the Difco RF slide test. The RF dipstick procedure was also tested with 50 serum samples confirmed positive by the Difco slide test. Of the 50 samples, 48 demonstrated positive results with the RF dipstick (see Table II). Five of the samples were tested by the quantitative procedure of Difco slide and the RF dipstick and were within 1 dilution with each of the samples tested.

TABLE II

| SPECIFICITY AND SENSITIVITY OF THE RF DIPSTICK | | |
|---|---|---|
| | SPECIFICITY | SENSITIVITY |
| Normal Population | 98/100 | |
| RF Positive Samples | | 48/50 |
| Percent | 98% | 96% |

EXAMPLE 6

A C-Reactive Protein (CRP) Test

This CRP test is a rapid latex screening test for qualitatively determining the presence or absence of C-Reactive Protein in human serum. C-Reactive Protein is found in serum of patients with inflammatory diseases. CRP has been characterized as a Beta-Globulin isolated and purified from human serum as one of many protein phenomena that occur in response to acute tissue injury.

A CRP stock reagent was prepared by adding 300 μl of anti-CRP, diluted in 2 ml of 0.85% NaCl, to 100 ml of Lytron 5252 latex suspension (48%) and was mixed for 1 hour. One mg of Human Gamma Globulin II, III (Sigma) was diluted in 1 ml of 0.85% NaCl and added to the stock latex suspension. The latex suspension was mixed for 1 hour and placed in a 56° C. water bath for 1 hour. The stock latex suspension was then mixed for 18–24 hours at room temperature. To the stock latex suspension, 0.4 gm of Brilliant Blue R dye (Sigma) was added and mixed for 2 hours.

A working reagent was prepared by adding 3.2 ml of yellow dye (Crescent) to 800 ml of 0.1M glycine buffer (GB) with 0.1% sodium azide and 240 mg of BSA. A 3.2 ml aliquot of CRP stock latex reagent was added to the 800 ml of GB and mixed for 1 hour. The working CRP dipstick latex reagent was stored at 2° C.–8° C.

The CRP latex reagent was tested with 15 serum samples from a normal population and 10 serum samples with a positive CRP. Of the 15 samples from a normal population, all 15 had negative results by the CRP dipsticks. Of the 10 CRP-positive serum samples, 10 were positive with the CRP dipstick (see Table III).

TABLE III

SPECIFICITY AND SENSITIVITY
OF THE CRP DIPSTICK REAGENT

|  | SPECIFICITY | SENSITIVITY |
| --- | --- | --- |
| Normal Samples | 15/15 |  |
| CRP-Positive Samples |  | 10/10 |
| Percent | 100% | 100% |

EXAMPLE 7

BTA Assay

A latex agglutination test was performed on urine for the detection of a bladder tumor analyte (BTA) associated with transitional cell carcinoma (TCC) of the bladder. BTA is a tumor marker isolated from the urine of individuals with TCC of the bladder. This analyte can be detected by the treated latex described below. If the BTA is present in freshly voided urine at a significant level and is mixed with the treated latex suspension (described below), it will combine with the latex particles to produce a visual color change and separation on a dipstick. The BTA is a peptide complex derived from the basal lamina, consisting of several specific derivatives of basement membrane constituent molecules.

A stock latex suspension was prepared by adding 12 mg of human IgG to 20 ml of saline solution and the solution was added to 750 ml of 48% solution of 0.25 micron latex particles. Two ml of normal goat serum was mixed with 18 ml of normal saline and added to the latex suspension. The stock latex suspension was heated at 56° C. for 1 hour and mixed. The latex suspension was allowed to cool to 30° C. and 1.88 gm of Brilliant Blue R dye was added and mixed for 18 hours at room temperature.

A working latex reagent was prepared by adding 1 gm of sodium azide, 1 gm of glycine, 1.5 gm of bovine serum albumin, 30 ml of water-soluble yellow dye and 105 ml of stock latex suspension to 3 liters of distilled water. The reagent was adjusted to pH 8.5 and mixed for 2 hours.

A 35 μl urine sample was mixed with 35 μl of the working latex reagent in a tube or well and a dipstick was added to the mixture.

To determine the specificity of the BTA assay, 71 urine samples were collected from patients with genitourinary disease or a normal population without bladder cancer. The samples were tested in duplicate. Of the 71 samples, 67 had a negative result, demonstrating a 94% specificity (Table IV).

To determine the sensitivity of the BTA assay, 25 urine samples with bladder cancer were tested. Of the 25 samples, 17 were positive with the BTA assay, demonstrating a 68% sensitivity (Table IV).

TABLE IV

SPECIFICITY AND SENSITIVITY OF THE BTA ASSAY

|  | SPECIFICITY | SENSITIVITY |
| --- | --- | --- |
| Non-Bladder Cancer | 67/71 |  |
| Bladder Cancer |  | 17/25 |
| Percent | 94% | 68% |

EXAMPLE 8

A Microalbumin Inhibition Assay

A stock reagent was prepared by adding 200 mg of N-hydroxysuccinimide and 200 mg of 1-ethyl-3-(3-dimethylaminopropyl) carbodiimide (Sigma) and mixing for 2 hours with 100 ml of Lytron 5251 or 601 latex suspension (Morton International). Human albumin, 100 mg (Sigma #1653), was added to the latex suspension and was mixed for 1 hour. The latex suspension was mixed for 18–24 hours at room temperature. Brilliant Blue R dye, 0.5 gm (Sigma), was added to the latex suspension and mixed rapidly for 1 hour.

A microalbumin working latex reagent was prepared by adding 3.2 ml of yellow water-soluble dye to 800 ml of 0.1M glycine buffer (GB), pH 8.2, with 0.1% sodium azide as a preservative. The stock latex reagent (3.2 ml) was added to the yellow GB. The working latex reagent was mixed for 1 hour with a magnetic stirrer.

Anti-human albumin (Sigma #A7544) was serial diluted and tested with the working reagent. It was determined that a 1:400 dilution in 0.1M glycine saline buffer was optimum for use.

In order to test the microalbumin latex reagent, human albumin was added to normal human urine at 1000 μg/ml and serial diluted in the same normal urine to less then 10 μg/ml of human albumin. Each of the diluted urine samples were tested by the following method:

1. A 10 μl sample of each of the urine samples was pipetted in a 12×75 mm polystyrene tube and 10 μl of a 1:400 anti-human albumin was added to the tube and mixed.
2. 65 μl of albumin working reagent was added to each tube and mixed.
3. A dipstick was added to each tube and the results were read after 15 seconds.
4. When the pad on the dipstick remains solid green, it indicates that there was sufficient albumin to inhibit the reaction between the albumin on the latex and the anti-albumin. Since the latex does not agglutinate, the latex (with blue dye) and yellow dye flow freely up the pad, thereby demonstrating a positive result.
5. When there was a color separation on the dipstick pad (showing blue on the bottom and yellow on the top), there was a reaction between the albumin of the latex (with blue dye) and the anti-albumin mixed with the samples. Accordingly, there was not sufficient albumin to inhibit the reaction, thereby demonstrating a negative result.

When the urine samples containing various amounts of albumin were tested, a positive result was obtained on samples with 33 µg/ml to 1000 µg/ml. Diabetic patients with 40 µg/ml or greater of albumin in their urine are considered diagnostically significant.

EXAMPLE 9

A BTA Dot-Enhanced Strip Assay

1. Construction of Strip

A dot-enhanced strip is prepared from the materials described in Example 1. The strip is constructed by applying a one-inch strip of Scotch transfer adhesive to the top edge of a 2"×11" polystyrene sheet. A 1"×10" piece of Ahlstrom 161 microporous material is pressed on the adhesive. Ten holes are punched one-inch apart in a 11"×1" polystyrene sheet. Wells are created in the polystyrene by making a depression below and adjacent to each hole so that the reagent and sample can be mixed before dispensing into the hole. The polystyrene with the holes is placed directly on top of the Ahlstrom 161. Circles (0.25") are punched out of a piece of Ahlstrom 161. The circles are collected and one is placed in the polystyrene. A well is placed below each circle on the polystyrene so that the reagent and sample can be mixed before dispensing to the circle.

2. Assay Procedure

One drop (50 µl) of latex reagent as described in Example 7 was added to a well on the strip containing one drop (50 µl) of urine sample and mixed. Two drops (100 µl) of the reagent sample mixture was transferred to the 0.25-inch hole containing a microporous dot. If the assay is positive (indicating the presence of BTA), the dot in the circle will be blue. If the sample does not contain BTA, the mixture will flow through the microporous dot onto the microporous pad below, and the dot will be a greenish yellow color.

3. BTA Strip Compared To BTA Latex Slide Assay

Samples of standards, analyte, normal urines, and TCC positive urines were tested with the BTA Strip test and the BTA Latex slide test. The strip test appears to be more sensitive with the standards and the analyte. See Table V.

TABLE V

COMPARISON OF STRIP VERSUS SLIDE ASSAY

| | STANDARDS | | | | | | | NORMAL URINES | | |
|---|---|---|---|---|---|---|---|---|---|---|
| | 0 | 2 | 5 | 10 | 15 | 20 | 40 | 200 | DEL | DE | JD |

RESULTS:

| | | | | | | | | | | | |
|---|---|---|---|---|---|---|---|---|---|---|---|
| STRIP | − | − | + | + | + | + | + | + | − | − | − |
| SLIDE | − | − | − | − | − | + | + | + | − | − | − |

| | ANALYTE | | | | TCC BLADDER URINES | | | |
|---|---|---|---|---|---|---|---|---|
| | 1/20 | 1/40 | 1/80 | AS | MU | MU 1/8 | MU 1/16 | MU 1/32 |

RESULTS:

| | | | | | | | | |
|---|---|---|---|---|---|---|---|---|
| STRIP | + | + | + | + | + | − | − | − |
| SLIDE | + | − | − | + | + | − | − | − |

EXAMPLE 10

RF Assay Using Washed Colloidal Textile Dye

A stock latex reagent was made by adding 5 mg of Human Gamma Globulin II, III to 100 ml of Lytron 601 latex suspension, as in Example I. This suspension was mixed for 1 hour at ambient temperature, placed in a water bath at 56° C. for an additional hour, and then mixed on a magnetic stirrer for 18 hours at ambient temperature. This latex concentrate is used as described below.

Dianix® Blue FBLN 200 (Hoechst Celanese, Charlotte, N.C.) was washed with water before use in the assay, as follows. A vigorously mixed 5% aqueous suspension of dye was centrifuged at 20,000×g for 30 minutes. The supernatant was decanted and discarded. The pellet was resuspended in an equal volume of water. The centrifugation and resuspension was repeated three more times. The final suspension was then centrifuged at 150×g for 30 minutes. Finally, the upper 80% of the supernatant was removed and well mixed before use.

The following ingredients were mixed well to yield 100 ml of latex working reagent: 97.2 ml of 0.1M glycine buffer, pH 8.2, 0.8 ml of glycine buffer containing 1% bovine serum albumin, 1.6 ml of dye suspension, and 0.4 ml of latex concentrate.

This reagent was used in conjunction with dipsticks prepared as described in Example 1. Assay format consisted of 65 µl of latex reagent and 5 µl serum. The positive control and three positive patient samples yielded positive results, that is, a dark blue band with white above. Three negative patient samples yielded negative results, observed as a uniform blue color throughout the viewing area of the dipstick.

Similar results were observed with Palanil® Brilliant Blue BGF 200% (BASF Corp., Charlotte, N.C.) prepared and used under similar conditions.

EXAMPLE 11

Assay for *Helicobacter pylori* Using Colloidal Dye

A latex reagent for the detection of *H. pylori* was prepared using detergent-free 0.25µ latex particles (Interfacial Dynamics Corp., Portland, Oreg.). a 1% suspension of latex was prepared in 20 mM phosphate buffer, pH 7.4. An equal volume of a solution of *H. pylori* antigen at 1 mg/ml was mixed into the latex, and the suspension was rotated at ambient temperature for two hours. The sensitized particles were washed twice by centrifugation at 10,000×g for 10 minutes, decanting the supernatant, and resuspending in an equal volume of buffer. The particles were blocked by rotation for 16 hours in 0.1M glycine buffered saline, pH 8.2, containing 0.2% bovine serum albumin.

A vigorously mixed 5% aqueous suspension of Brilliant Blue R was centrifuged at 25,000×g for 30 minutes. The upper 75% of the supernatant was carefully removed and mixed well before use. To 1.7 ml of 1% sensitized particles, was added 3.4 µl of dye suspension, and then mixed by continuous rotation for two hours at ambient temperature. Finally, the particles were diluted to a final concentration of 0.2% with 0.1M glycine buffered saline to yield the working reagent.

This reagent was used in a dipstick assay format identical to that described in Example 10. The dipstick assay was used to test nine positive and nine negative serum samples, as previously determined by enzyme immunoassay. Eight of the nine positives tested positive, with one equivocal, while all nine negatives tested negative.

EXAMPLE 12

RF Assay with Background-Enhancing Colloidal Textile Dye on the Pad

The RF reagent was prepared with Dianix® Blue FBLN 200, but with no background-enhancing dye, as in Example 10. Before the fiberglass (Whatman Specialty Products, Fairfield, N.J.; lot no. PD008-13A60) was attached to the dipstick, it was immersed in an ethanol solution of thoroughly washed Dianix® Brilliant Yellow H10GF (Hoechst Celanese) (250 mg dye/dl ethanol). The dyed fiberglass was then air dried in a fume hood at ambient temperature, followed by mounting on the dipstick backing.

Using the same assay format as in Example 10, positive and negative control samples were assayed. The results observed with the yellow colloidal dye in the fiberglass were identical to those observed with a yellow water-soluble background-enhancing dye in the latex reagent. Movement of the aqueous assay buffer does not cause migration of the previously dried colloidal dye.

From the foregoing, it will be appreciated that, although specific embodiments of the invention have been described herein for purposes of illustration, various modifications may be made without deviating from the spirit and scope of the invention.

I claim:

1. A method for determining the presence of a substance in a biological fluid, comprising the steps of:
   (a) incubating a biological fluid suspected of containing said substance with a mixture of a suspension of unattached colloidal dye and latex particles having a binding partner to said substance bound thereto, said latex particles having colloidal dye directly or indirectly attached thereto or both, to form a reaction mixture wherein latex particles binding said substance agglutinate, and wherein at least some unattached colloidal dye within said suspension is entrapped as a result of said agglutination;
   (b) contacting said reaction mixture with a microporous pad which permits differential migration of non-agglutinated latex particles versus agglutinated latex particles; and
   (c) detecting the presence of said colloidal dye associated with said agglutinated latex particles, and therefrom determining the presence of said substance.

2. A direct latex agglutination test kit for determining the presence of a substance in a biological fluid, comprising:
   (a) a mixture of a suspension of unattached colloidal dye and latex particles having a binding partner to said substance bound thereto, said latex particles having colloidal dye directly or indirectly attached thereto or both; and
   (b) a microporous pad which permits differential migration of non-agglutinated latex particles versus agglutinated latex particles.

3. A method for determining the presence of a substance in a biological fluid, comprising the steps of:
   (a) incubating a biological fluid suspected of containing said substance with a binding partner to said substance, to form a first reaction mixture;
   (b) incubating said first reaction mixture with a mixture of a suspension of unattached colloidal dye and latex particles having said substance bound thereto, said latex particles having colloidal dye attached directly or indirectly thereto or both, to form a second reaction mixture wherein latex particles binding said binding partner agglutinate, and wherein at least some unattached colloidal dye within said suspension is entrapped as a result of said agglutination;
   (c) contacting said second reaction mixture with a microporous pad which permits differential migration of non-agglutinated latex particles versus agglutinated latex particles; and
   (d) detecting the presence of said colloidal dye associated with said agglutinated latex particles, and therefrom determining the presence of said substance.

4. An indirect latex agglutination test kit for determining the presence of a substance in a biological fluid, comprising:
   (a) a binding partner to said substance;
   (b) a mixture of a suspension of unattached colloidal dye and latex particles having said substance bound thereto or both, said latex particles having colloidal dye directly or indirectly attached thereto; and
   (c) a microporous pad which permits differential migration of non-agglutinated latex particles versus agglutinated latex particles.

5. A method for determining the presence of a bladder tumor analyte associated with transitional cell carcinoma, comprising the steps of:
   (a) incubating a biological fluid suspected of containing said bladder tumor analyte associated with transitional cell carcinoma with a mixture of a suspension of unattached colloidal dye and latex particles having a blocking protein bound thereto, said latex particles having colloidal dye directly or indirectly attached thereto or both, to form a reaction mixture wherein latex particles binding said analyte agglutinate, and wherein at least some unattached colloidal dye within said suspension is entrapped as a result of said agglutination;
   (b) contacting said reaction mixture with a microporous pad which permits differential migration of non-agglutinated latex particles versus agglutinated latex particles; and
   (c) detecting the presence of said colloidal dye associated with said agglutinated latex particles, and therefrom determining the presence of said analyte.

6. A direct latex agglutination test kit for determining the presence of a bladder tumor analyte associated with transitional cell carcinoma, comprising:
   (a) a mixture of a suspension of unattached colloidal dye and latex particles having a blocking protein bound thereto, said latex particles having colloidal dye directly or indirectly attached thereto or both; and
   (b) a microporous pad which permits differential migration of non-agglutinated latex particles versus agglutinated latex particles.

7. A method for determining the presence of a substance in a biological fluid, comprising the steps of:
   (a) incubating a biological fluid suspected of containing said substance, latex particles having a first colloidal dye attached thereto, and a mixture of a suspension of unattached second colloidal dye and latex particles having a binding partner to said substance bound thereto and having second colloidal dye attached directly or indirectly thereto or both, said first colloidal dye and said second colloidal dye being contrasting in color, to form a reaction mixture wherein latex particles binding said substance agglutinate, and wherein at least some unattached second colloidal dye within said suspension is entrapped as a result of said agglutination;

(b) contacting said reaction mixture with a microporous pad which permits differential migration of non-agglutinated latex particles versus agglutinated latex particles; and (c) detecting the presence of said second colloidal dye associated with said agglutinated latex particles, and therefrom determining the presence of said substance.

8. A direct latex agglutination test kit for determining the presence of a substance in a biological fluid, comprising:

(a) latex particles having a first colloidal dye attached thereto;

(b) a mixture of a suspension of unattached second colloidal dye and latex particles having a binding partner to said substance bound thereto and having second colloidal dye attached directly or indirectly thereto or both, said first colloidal dye and said second colloidal dye being contrasting in color; and (c) a microporous pad which permits differential migration of non-agglutinated latex particles versus agglutinated latex particles.

9. A method for determining the presence of a substance in a biological fluid, comprising the steps of:

(a) incubating a biological fluid suspected of containing said substance with a binding partner to said substance, to form a first reaction mixture;

(b) incubating said first reaction mixture with latex particles having a first colloidal dye attached thereto and a mixture of a suspension of unattached second colloidal dye and latex particles having said substance bound thereto and having second colloidal dye attached directly or indirectly thereto or both, said first colloidal dye and said second colloidal dye being contrasting in color, to form a second reaction mixture wherein latex particles binding said binding partner agglutinate, and wherein at least some unattached second colloidal dye within said suspension is entrapped as a result of said agglutination;

(c) contacting said second reaction mixture with a microporous pad which permits differential migration of non-agglutinated latex particles versus agglutinated latex particles; and (d) detecting the presence of said second colloidal dye associated with said agglutinated latex particles, and therefrom determining the presence of said substance.

10. An indirect latex agglutination test kit for determining the presence of a substance in a biological fluid, comprising:

(a) a binding partner to said substance;

(b) latex particles having a first colloidal dye attached thereto;

(c) a mixture of a suspension of unattached second colloidal dye and latex particles having said substance bound thereto and having second colloidal dye attached directly or indirectly thereto or both, said first colloidal dye and said second colloidal dye being contrasting in color; and (d) a microporous pad which permits differential migration of non-agglutinated latex particles versus agglutinated latex particles.

11. A method for determining the presence of a substance in a biological fluid, comprising the steps of:

(a) incubating a biological fluid suspected of containing said substance with a mixture of a suspension of unattached colloidal dye and latex particles having a binding partner to said substance bound thereto, said latex particles having colloidal dye directly or indirectly attached thereto or both, to form a reaction mixture wherein latex particles binding said substance agglutinate, and wherein at least some unattached colloidal dye within said suspension is entrapped as a result of said agglutination;

(b) contacting said reaction mixture with a microporous pad to which is attached a non-water-soluble background-enhancing dye that is contrasting in color to said colloidal dye, said microporous pad permitting differential migration of non-agglutinated latex particles versus agglutinated latex particles; and (c) detecting the presence of said colloidal dye associated with said agglutinated latex particles, and therefrom determining the presence of said substance.

12. A direct latex agglutination test kit for determining the presence of a substance in a biological fluid, comprising:

(a) a mixture of a suspension of unattached colloidal dye and latex particles having a binding partner to said substance bound thereto, said latex particles having colloidal dye directly or indirectly attached thereto or both; and (b) a microporous pad to which is attached a non-water-soluble background-enhancing dye that is contrasting in color to said colloidal dye, said microporous pad permitting differential migration of non-agglutinated latex particles versus agglutinated latex particles.

13. A method for determining the presence of a substance in a biological fluid, comprising the steps of:

(a) incubating a biological fluid suspected of containing said substance with a binding partner to said substance, to form a first reaction mixture;

(b) incubating said first reaction mixture with a mixture of a suspension of unattached colloidal dye and latex particles having said substance bound thereto, said latex particles having colloidal dye directly or indirectly attached thereto or both, to form a second reaction mixture wherein latex particles binding said binding partner agglutinate, and wherein at least some unattached colloidal dye within said suspension is entrapped as a result of said agglutination;

(c) contacting said second reaction mixture with a microporous pad to which is attached a non-water-soluble background-enhancing dye that is contrasting in color to said colloidal dye, said microporous pad permitting differential migration of non-agglutinated latex particles versus agglutinated latex particles; and (d) detecting the presence of said colloidal dye associated with said agglutinated latex particles, and therefrom determining the presence of said substance.

14. An indirect latex agglutination test kit for determining the presence of a substance in a biological fluid, comprising:

(a) a binding partner to said substance;

(b) a mixture of a suspension of unattached colloidal dye and latex particles having said substance bound thereto, said latex particles having colloidal dye directly or indirectly attached thereto or both; and (c) a microporous pad to which is attached a non-water-soluble background-enhancing dye that is contrasting in color to said colloidal dye, said microporous pad permitting differential migration of non-agglutinated latex particles versus agglutinated latex particles.

15. A method for determining the presence of a bladder tumor analyte associated with transitional cell carcinoma, comprising the steps of:

(a) incubating a biological fluid suspected of containing said bladder tumor analyte associated with transitional cell carcinoma with a mixture of a suspension of unattached colloidal dye and latex particles having a blocking protein bound thereto, said latex particles having colloidal dye directly or indirectly attached thereto or both, to form a reaction mixture wherein latex particles binding said analyte agglutinate, and wherein at least some unattached colloidal dye within said suspension is entrapped as a result of said agglutination;

(b) contacting said reaction mixture with a microporous pad to which is attached a non-water-soluble background-enhancing dye that is contrasting in color to said colloidal dye, said microporous pad permitting differential migration of non-agglutinated latex particles versus agglutinated latex particles; and (c) detecting the presence of said colloidal dye associated with said agglutinated latex particles, and therefrom determining the presence of said analyte.

16. A direct latex agglutination test kit for determining the presence of a bladder tumor analyte associated with transitional cell carcinoma, comprising:

(a) a mixture of a suspension of unattached colloidal dye and latex particles having a blocking protein bound thereto, said latex particles having colloidal dye directly or indirectly attached thereto or both; and (b) a microporous pad to which is attached a non-water-soluble background-enhancing dye that is contrasting in color to said colloidal dye, said microporous pad permitting differential migration of non-agglutinated latex particles versus agglutinated latex particles.

17. A method for determining the presence of a substance in a biological fluid, comprising the steps of:

(a) incubating a water-soluble background-enhancing dye, a biological fluid suspected of containing said substance, and a mixture of a suspension of unattached colloidal dye and latex particles having a binding partner to said substance bound thereto, said latex particles having colloidal dye directly or indirectly attached thereto or both, said colloidal dye and said background-enhancing dye being contrasting in color, to form a reaction mixture wherein latex particles binding said substance agglutinate, and wherein at least some unattached colloidal dye within said suspension is entrapped as a result of said agglutination;

(b) contacting said reaction mixture with a microporous pad which permits differential migration of non-agglutinated latex particles and background-enhancing dye versus agglutinated latex particles; and (c) detecting the presence of said colloidal dye associated with said agglutinated latex particles, and therefrom determining the presence of said substance.

18. A direct latex agglutination test kit for determining the presence of a substance in a biological fluid, comprising:

(a) a water-soluble background-enhancing dye;

(b) a mixture of a suspension of unattached colloidal dye and latex particles having a binding partner to said substance bound thereto, said latex particles having colloidal dye directly or indirectly attached thereto or both, said colloidal dye and said background-enhancing dye being contrasting in color; and (c) a microporous pad which permits differential migration of non-agglutinated latex particles and background-enhancing dye versus agglutinated latex particles.

19. A method for determining the presence of a substance in a biological fluid, comprising the steps of:

(a) incubating a water-soluble background-enhancing dye, a biological fluid suspected of containing said substance, and a binding partner to said substance, to form a first reaction mixture;

(b) incubating said first reaction mixture with a mixture of a suspension of unattached colloidal dye and latex particles having said substance bound thereto, said latex particles having colloidal dye directly or indirectly attached thereto or both, said colloidal dye and said background-enhancing dye being contrasting in color, to form a second reaction mixture wherein latex particles binding said binding partner agglutinate, and wherein at least some unattached colloidal dye within said suspension is entrapped as a result of said agglutination;

(c) contacting said second reaction mixture with a microporous pad which permits differential migration of non-agglutinated latex particles and background-enhancing dye versus agglutinated latex particles; and (d) detecting the presence of said colloidal dye associated with said agglutinated latex particles, and therefrom determining the presence of said substance.

20. An indirect latex agglutination test kit for determining the presence of a substance in a biological fluid, comprising:

(a) a binding partner to said substance;

(b) a water-soluble background-enhancing dye;

(c) a mixture of a suspension of unattached colloidal dye and latex particles having said substance bound thereto, said latex particles having colloidal dye directly or indirectly attached thereto or both, said colloidal dye and said background-enhancing dye being contrasting in color; and (d) a microporous pad which permits differential migration of non-agglutinated latex particles and background-enhancing dye versus agglutinated latex particles.

21. A method for determining the presence of a bladder tumor analyte associated with transitional cell carcinoma, comprising the steps of:

(a) incubating a water-soluble background-enhancing dye, a biological fluid suspected of containing said bladder tumor analyte associated with transitional cell carcinoma, and a mixture of a suspension of unattached colloidal dye and latex particles having a blocking protein bound thereto, said latex particles having colloidal dye directly or indirectly attached thereto or both, said colloidal dye and said background-enhancing dye being contrasting in color, to form a reaction mixture wherein latex particles binding said analyte agglutinate, and wherein at least some unattached colloidal dye within said suspension is entrapped as a result of said agglutination;

(b) contacting said reaction mixture with a microporous pad which permits differential migration of non-agglutinated latex particles and background-enhancing dye versus agglutinated latex particles; and (c) detecting the presence of said colloidal dye associated with said agglutinated latex particles, and therefrom determining the presence of said analyte.

22. A direct latex agglutination test kit for determining the presence of a bladder tumor analyte associated with transitional cell carcinoma, comprising:
  (a) a water-soluble background-enhancing dye;
  (b) a mixture of a suspension of unattached colloidal dye and latex particles having a blocking protein bound thereto, said latex particles having colloidal dye directly or indirectly attached thereto or both, said colloidal dye and said background-enhancing dye being contrasting in color; and
  (c) a microporous pad which permits differential migration of non-agglutinated latex particles and background-enhancing dye versus agglutinated latex particles.

* * * * *